United States Patent
Knudsen et al.

(10) Patent No.: US 6,569,832 B1
(45) Date of Patent: May 27, 2003

(54) INHIBITION OF BETA CELL DEGENERATION

(75) Inventors: Liselotte Bjerre Knudsen, Valby (DK); Carsten Foged Godtfredsen, Herlev (DK); Jacob Sten Petersen, Copenhagen (DK); Richard David Carr, Vaerlose (DK); Søren Bregenholt, Copenhagen (DE)

(73) Assignee: Novo Nordisk A/S, Bagsvaerd (DK)

( * ) Notice: Subject to any disclaimer, the term of this patent is extended or adjusted under 35 U.S.C. 154(b) by 84 days.

(21) Appl. No.: 09/709,856

(22) Filed: Nov. 10, 2000

Related U.S. Application Data

(60) Provisional application No. 60/166,800, filed on Nov. 22, 1999, and provisional application No. 60/185,845, filed on Feb. 29, 2000.

(30) Foreign Application Priority Data

Nov. 12, 1999 (DK) ........................................ 1999 01628
Feb. 22, 2000 (DK) ........................................ 2000 00270

(51) Int. Cl.$^7$ ............................................... A16K 38/00
(52) U.S. Cl. .......................................... 514/12; 530/308
(58) Field of Search ............................. 514/12; 530/308

(56) References Cited

U.S. PATENT DOCUMENTS 5,614,492 A  3/1997  Habener ...................... 514/12

FOREIGN PATENT DOCUMENTS

| DE | 199 21 537 | 11/2000 |
|----|------------|---------|
| WO | WO 97/29180 | 8/1997 |
| WO | WO 98/08871 A | 3/1998 |
| WO | WO 00/07617 | 2/2000 |

OTHER PUBLICATIONS

CA 132:73479 (1999).*
CA 131:281647 (1999).*
CA 127:104621 (1997).*
CA 125:105510 (1996).*
CA 125:318134 (1996).*
English Translation of: Waeber, G. "Dysfonctinos de la cellule beta–pacreatique observees lors de diabete non–insulino–dependant" Revue Medicale De La Suisse Romande, vol. 113, pp. 695–698 (1993).
Byrne, et al., Database Medline (online) US National Library of Medicine–"Glucagon–Like Peptide 1 Improves The Ability Of The Beta–Cell To Sense And Respond To Glucose In Subjects With Impaired Glucose Tolerance". Accession No. 09595988 & Database accession No. 98366886 Abstract & Diabetes vol. 47, No. 8, pp. 1259–1265 (Aug. 1998).
Edvell A. et al., "Initiation Of Increased Pancreatic Islet Growth In Young Normoglycemic Mice (Ummea +/?)" Endocrinology, vol. 140, No. 2, pp. 778–783 (1999).
Xu et al (1999) Diabetes. 48:2270–2276.
Holst (1999) Expert Opinion on Investigational Drugs 8:1409–1415.
Wang et al (1997) J. Clin. Invest. 99: 2883–2889.
Britsch et al (1996) Acta. Physiol. Scand. 157: 353.
Rachman et al (1996) Diabetes. 45: 1524–1530.

* cited by examiner

*Primary Examiner*—Sheela Huff
(74) *Attorney, Agent, or Firm*—Reza Green, Esq.; Richard W. Bork, Esq.; Marc A. Began, Esq.

(57) ABSTRACT

This invention relates to a method for modulating, inhibiting or decreasing or preventing beta cell degeneration, loss of beta cell function, beta cell dysfunction, and/or death of beta cells, such as necrosis or apoptosis of beta cells in a subject comprising administering a GLP-1 agonist to said subject.

18 Claims, 3 Drawing Sheets

Fraction of beta-cells in proliferation.

Fraction of beta-cells in proliferation.

Volume fractions of beta-cells, nonbeta-cells, and islets related to total pancreas volume.

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic
<221> NAME/KEY: MUTAGEN
<222> LOCATION: 2
<223> OTHER INFORMATION: Xaa = Ala, Gly, Ser, Thr, Leu, Ile, Val, Glu
      Asp, Met or Lys
<221> NAME/KEY: MUTAGEN
<222> LOCATION: 3
<223> OTHER INFORMATION: Xaa = Glu, Asp, or Lys
<221> NAME/KEY: MUTAGEN
<222> LOCATION: 5
<223> OTHER INFORMATION: Xaa =Thr, Ala, Gly, Ser, Leu, Ile, Val, Glu,
      Asp, or Lys
<221> NAME/KEY: MUTAGEN
<222> LOCATION: 8
<223> OTHER INFORMATION: Xaa = Ser, Ala, Gly, Thr, Leu, Ile, Val, Glu,
      Asp, or Lys
<221> NAME/KEY: MUTAGEN
<222> LOCATION: 10
<223> OTHER INFORMATION: Xaa = Val, Ala, Gly, Ser, Thr, Leu, Ile, Tyr,
      Glu, Asp, or Lys
<221> NAME/KEY: MUTAGEN
<222> LOCATION: 11
<223> OTHER INFORMATION: Xaa = Ser, Ala, Gly, Thr, Leu, Ile, Val, Glu,
      Asp or Lys
<221> NAME/KEY: MUTAGEN
<222> LOCATION: 12
<223> OTHER INFORMATION: Xaa = Ser, Ala, Gly, Thr, Leu, Ile, Val, Glu,
      Asp, or Lys
<221> NAME/KEY: MUTAGEN
<222> LOCATION: 13
<223> OTHER INFORMATION: Xaa = Tyr, Phe, Trp, Glu, Asp, or Lys
<221> NAME/KEY: MUTAGEN
<222> LOCATION: 14
<223> OTHER INFORMATION: Xaa = Leu, Ala, Gly, Ser, Thr, Leu, Ile, Val,
      Glu, Asp, or Lys
<221> NAME/KEY: MUTAGEN
<222> LOCATION: 15
<223> OTHER INFORMATION: Xaa = Glu, Asp, or Lys
<221> NAME/KEY: MUTAGEN
<222> LOCATION: 16
<223> OTHER INFORMATION: Xaa = Gly, Ala, Ser, Thr, Leu, Ile, Val, Glu,
      Asp, or Lys
<221> NAME/KEY: MUTAGEN
<222> LOCATION: 17
<223> OTHER INFORMATION: Xaa = Gln, Asn, Arg, Glu, Asp, or Lys
<221> NAME/KEY: MUTAGEN
<222> LOCATION: 18
<223> OTHER INFORMATION: Xaa = Ala, Gly, Ser, Thr, Leu, Ile, Val, Arg,
      Glu, Asp, or Lys
<221> NAME/KEY: MUTAGEN
<222> LOCATION: 19
<223> OTHER INFORMATION: Xaa = Ala, Gly, Ser, Thr, Leu, Ile, Val, Glu,
      Asp, or Lys
<221> NAME/KEY: MUTAGEN
<222> LOCATION: 20
<223> OTHER INFORMATION: Xaa = Lys, Arg, Gln, Glu, Asp or His
<221> NAME/KEY: MUTAGEN
<222> LOCATION: 21
<223> OTHER INFORMATION: Xaa = Glu, Asp or Lys
<221> NAME/KEY: MUTAGEN
<222> LOCATION: 24
<223> OTHER INFORMATION: Xaa = Ala, Gly, Ser, Thr, Leu, Ile, Val, Glu,
      Asp, or Lys
<221> NAME/KEY: MUTAGEN
<222> LOCATION: 25
<223> OTHER INFORMATION: Xaa =Trp, Phe, Tyr, Glu, Asp, or Lys
<221> NAME/KEY: MUTAGEN
<222> LOCATION: 26
<223> OTHER INFORMATION: Xaa = Leu, Gly, Ala, Ser, Thr, Ile, Val, Glu,

```
        Asp, or Lys
<221> NAME/KEY: MUTAGEN
<222> LOCATION: 27
<223> OTHER INFORMATION: Xaa = Val, Gly, Ala, Ser, Thr, Leu, Ile, Glu,
        Asp, or Lys
<221> NAME/KEY: MUTAGEN
<222> LOCATION: 28
<223> OTHER INFORMATION: Xaa = Lys, Arg, Glu, Asp, or His
<221> NAME/KEY: MUTAGEN
<222> LOCATION: 29
<223> OTHER INFORMATION: Xaa = Gly, Ala, Ser, Thr, Leu, Ile, Val, Glu,
        Asp or Lys
<221> NAME/KEY: MUTAGEN
<222> LOCATION: 30
<223> OTHER INFORMATION: Xaa = Arg, Lys, Glu, Asp, or His
<221> NAME/KEY: MUTAGEN
<222> LOCATION: 31
<223> OTHER INFORMATION: Xaa = Gly, Ala, Ser, Thr, Leu, Ile, Val, Glu,
        Asp, or Lys or is deleted
<221> NAME/KEY: MUTAGEN
<222> LOCATION: 32
<223> OTHER INFORMATION: Xaa = Arg, Lys, Glu, Asp, or His, or is deleted
<221> NAME/KEY: MUTAGEN
<222> LOCATION: 33
<223> OTHER INFORMATION: Xaa = Arg, Lys, Glu, Asp, or His, or is deleted
<221> NAME/KEY: MUTAGEN
<222> LOCATION: 34
<223> OTHER INFORMATION: Xaa = Asp, Glu, or Lys, or is deleted
<221> NAME/KEY: MUTAGEN
<222> LOCATION: 35
<223> OTHER INFORMATION: Xaa = Phe, Trp, Tyr, Glu, Asp, or Lys, or is
        deleted
<221> NAME/KEY: MUTAGEN
<222> LOCATION: 36
<223> OTHER INFORMATION: Xaa = Pro, Lys, Glu, or Asp, or is deleted
<221> NAME/KEY: MUTAGEN
<222> LOCATION: 37
<223> OTHER INFORMATION: Xaa = Glu, Asp, or Lys, or is deleted
<221> NAME/KEY: MUTAGEN
<222> LOCATION: 38
<223> OTHER INFORMATION: Xaa = Glu, Asp, or Lys, or is deleted
<221> NAME/KEY: MUTAGEN
<222> LOCATION: 39
<223> OTHER INFORMATION: Xaa = Val, Glu, Asp, or Lys, or is deleted

<400> SEQUENCE: 1

His Xaa Xaa Gly Xaa Phe Thr Xaa Asp Xaa Xaa Xaa Xaa Xaa Xaa Xaa
 1               5                   10                  15

Xaa Xaa Xaa Xaa Xaa Phe Ile Xaa Xaa Xaa Xaa Xaa Xaa Xaa Xaa
            20                  25                  30

Xaa Xaa Xaa Xaa Xaa Xaa Xaa
        35
```

INHIBITION OF BETA CELL DEGENERATION

CROSS-REFERENCE TO RELATED APPLICATIONS

This application claims priority under 35 U.S.C. 119 of Danish application no. PA 1999 01628 filed on Nov. 12, 1999, Danish application no. PA 2000 00270 filed on Feb. 22, 2000, U.S. provisional application no. 60/166,800 filed on Nov. 22, 1999 and U.S. provisional application Serial no. 60/185,845 filed on Feb. 29, 2000, the contents of which are fully incorporated herein by reference.

The present invention relates to a method for modulating, inhibiting or decreasing or preventing beta cell degeneration, loss of beta cell function, beta cell dysfunction, and/or death of beta cells, such as necrosis or apoptosis of beta cells in a subject comprising administering a GLP-1 agonist to said subject.

BACKGROUND

What most textbooks of pathology describe as cell death is coagulative necrosis. This is an abnormal morphological appearance, detected in tissue examined under the microscope. The changes, which affect aggregates of adjacent cells or functionally related cohorts of cells, are seen in a variety of contexts produced by accident, injury, or disease. Among the environmental perturbations that may cause cell necrosis are oxygen deprivation (anoxia), hyperthermia, immunological attack, and exposure to various toxins that inhibit crucial intracellular metabolic processes. Coagulative necrosis is the classical form of cell change seen when tissues autolyze (digest themselves) in vitro.

Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammalians the beta-cell mass is submitted to dynamic changes to adapt insulin production for maintaining euglycemia in particular conditions, such as pregnancy and obesity (J. Dev. Physiol. 5: 373, 1983 and Endocrinology 130: 1459, 1992). The control of beta cell mass depends on a subtle balance between cell proliferation, growth and cell death (apoptosis). A disruption of this balance may lead to impairment of glucose homeostasis. For example, it is noteworthy that glucose intolerance develops with aging when beta cell replication rates are reduced (Diabetes 32: 14, 1983) and human autopsy studies repeatedly showed a 40–60% reduction of beta cell mass in patients with non-insulin-dependent-diabetes mellitus compared with nondiabetic subjects (Am. J. Med. 70: 105, 1981 and Diabetes Res. 9: 151, 1988). It is generally agreed that insulin resistance is an invariable accompaniment of obesity but that normoglycemia is maintained by compensatory hyperinsulinemia until the beta cells become unable to meet the increased demand for insulin, at which point Type 2 Diabetes begins.

Apoptosis is also associated with diseases states such as cancer, immunological disorders, like multiple sclerosis, and AIDS, and neurodegenerative disorders (Science 267: 1449, 995), like Alzheimers disease, stroke, and Parkinson's disease.

DESCRIPTION OF THE INVENTION

Figure 1:
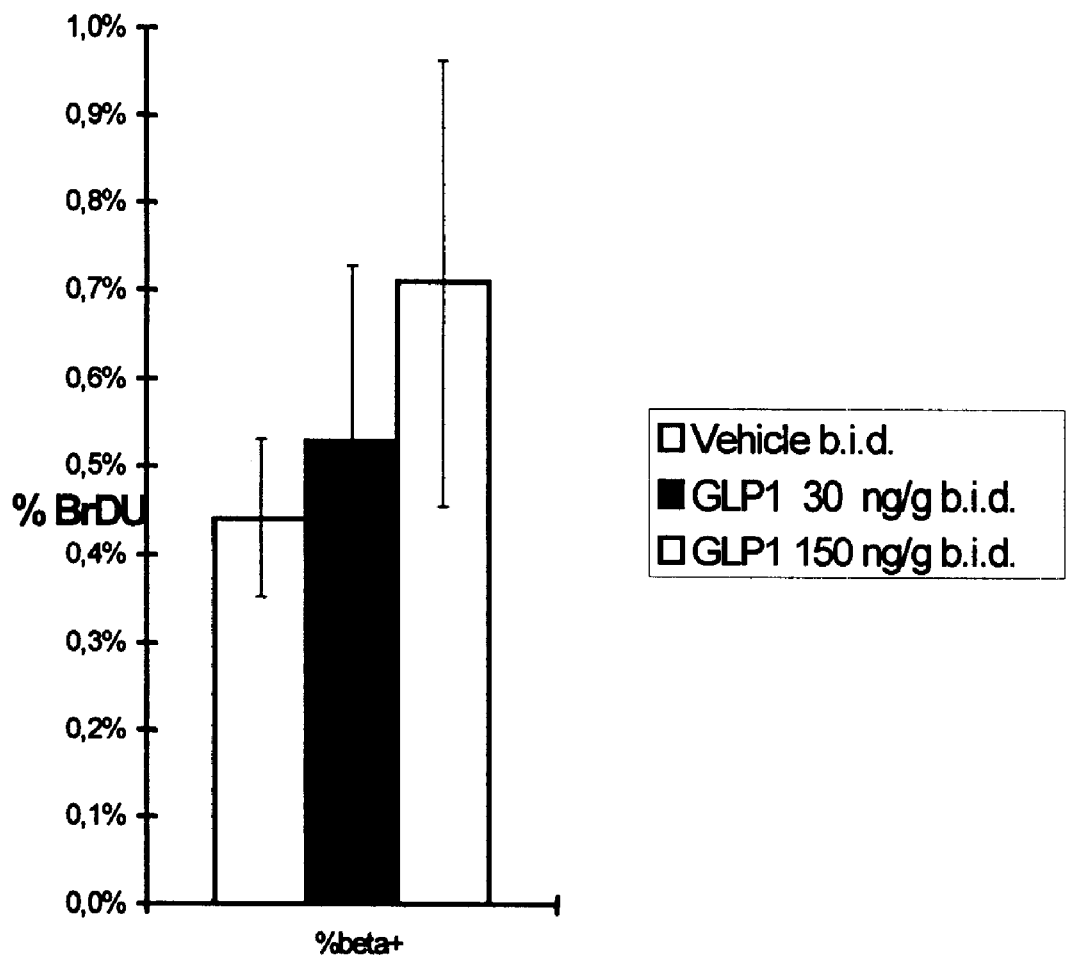
FIG. 1 shows a dose dependent increase in the percentage of Bromodeoxyuridine (BrDU) positive beta-cells in the pancreases of Zucker Diabetic Fatty ("ZDF") rats treated with vehicle, 30 ug/g $Arg^{34}$, $Lys^{26}$(N-ε-(γ-Glu(N-α-hexadecanoyl)))-GLP-1(7–37) ("GLP-1") or 150 ug/g GLP-1.

Accordingly, the present invention relates to use of a GLP-1 agonist for the preparation of a medicament for treatment of beta cell degeneration, such as necrosis or apoptosis of β-cells.

Furthermore, the present invention relates to use of a GLP-1 agonist for the preparation of a medicament for modulation of beta cell degeneration, such as necrosis or apoptosis of β-cells.

Furthermore, the present invention relates to use of a GLP-1 agonist for the preparation of a medicament for inhibition of beta cell degeneration, such as necrosis or apoptosis of β-cells.

Furthermore, the present invention relates to use of a GLP-1 agonist for the preparation of a medicament for decreasing beta cell degeneration, such as necrosis or apoptosis of β-cells.

Furthermore, the present invention relates to use of a GLP-1 agonist for the preparation of a medicament for reduction of beta cell degeneration, such as necrosis or apoptosis of β-cells.

Furthermore, the present invention relates to use of a GLP-1 agonist for the preparation of a medicament for arresting beta cell degeneration, such as necrosis or apoptosis of β-cells.

Furthermore, the present invention relates to use of a GLP-1 agonist preventing beta cell degeneration for the preparation of a medicament for prevention of beta cell degeneration, such as necrosis or apoptosis of β-cells.

Moreover, the invention relates to a method for treatment of beta cell degeneration, such as necrosis or apoptosis of β-cells, in a subject comprising administering a GLP-1 agonist to said subject.

Furthermore, the invention relates to a method for modulation of beta cell degeneration, such as necrosis or apoptosis of β-cells, in a subject comprising administering a GLP-1 agonist to said subject.

Furthermore, the invention relates to a method for inhibition of beta cell degeneration, such as necrosis or apoptosis of β-cells, in a subject comprising administering a GLP-1 agonist to said subject.

Furthermore, the invention relates to a method for decreasing beta cell degeneration, such as necrosis or apoptosis of β-cells, in a subject comprising administering a GLP-1 agonist to said subject.

Furthermore, the invention relates to a method for reduction of beta cell degeneration, such as necrosis or apoptosis of β-cells, in a subject comprising administering a GLP-1 agonist to said subject.

Furthermore, the invention relates to a method for arresting beta cell degeneration, such as necrosis or apoptosis of β-cells, in a subject comprising administering a GLP-1 agonist to said subject.

Furthermore, the invention relates to a method for prevention of beta cell degeneration, such as necrosis or apoptosis of β-cells, in a subject comprising administering a GLP-1 agonist to said subject.

In one embodiment of the invention beta cell degeneration is necrosis of beta cells.

In another embodiment of the invention beta cell degeneration is apoptosis of beta cells. In a further embodiment said apoptosis is induced by a cytokine. The cytokine may be any cytokine or mixtures thereof, such as interleukin 1 (IL-1), IL-2, IL-3, IL-5, IL-6, IL-7, IL-8, IL-9, IL-12, IL-14, IL-17, interferon-γ, tumor necrosis factor-α, TNF-β, granulocyte macrophage colony stimulating factor, monocyte chemoattractant protein-1, or mixtures thereof.

The subject is preferably a mammal, more preferably a human.

The use according any of the above uses in a regimen which additionally comprises treatment with human growth hormone, a growth hormone releasing agent or a growth factor such as prolactin or placental lactogen; the use of human growth hormone, a growth hormone releasing agent or a growth factor such as prolactin or placental lactogen for the preparation of a medicament for inhibiting the beta cell degeneration, such as necrosis or apoptosis of β-cells in a subject; the use of human growth hormone, a growth hormone releasing agent or a growth factor such as prolactin or placental lactogen for the preparation of a medicament for treatment of beta cell degeneration, such as necrosis or apoptosis of β-cells in a subject.

In one embodiment of the invention the GLP-1 agonist is GLP-1(7–37) or GLP-1(7–36) amide.

In a further embodiment of the invention the GLP-1 agonist is a GLP-1 analogue.

In a further embodiment of the invention the GLP-1 analogue is selected from the Thr$^8$, Met$^8$, Gly$^8$ and Val$^8$ analogues of GLP-1(7–37) and GLP-1(7–36) amide, m the Gly$^8$ and Val$^8$ analogues of GLP-1(7–37) and GLP-1(7–36) amide, most preferred the Val$^8$ analogues of GLP-1(7–37) and GLP-1(7–36) amide.

In a further embodiment of the invention the GLP-1 analogue has the formula (SEQ ID NO: 1) II:

```
 7   8   9  10  11  12  13  14  15  16  17      (II)
His-Xaa-Xaa-Gly-Xaa-Phe-Thr-Xaa-Asp-Xaa-Xaa- 18  19  20  21  22  23  24  25  26  27  28
Xaa-Xaa-Xaa-Xaa-Xaa-Xaa-Xaa-Xaa-Xaa-Xaa-Phe- 29  30  31  32  33  34  35  36  37  38
Ile-Xaa-Xaa-Xaa-Xaa-Xaa-Xaa-Xaa-Xaa-Xaa 39  40  41  42  43  44  45
Xaa-Xaa-Xaa-Xaa-Xaa-Xaa-Xaa
``` wherein

Xaa at position 8 is Ala, Gly, Ser, Thr, Leu, Ile, Val, Glu, Asp, Met, or Lys,

Xaa at position 9 is Glu, Asp, or Lys,

Xaa at position 11 is Thr, Ala, Gly, Ser, Leu, Ile, Val, Glu, Asp, or Lys,

Xaa at position 14 is Ser, Ala, Gly, Thr, Leu, Ile, Val, Glu, Asp, or Lys,

Xaa at position 16 is Val, Ala, Gly, Ser, Thr, Leu, Ile, Tyr, Glu, Asp, or Lys,

Xaa at position 17 is Ser, Ala, Gly, Thr, Leu, Ile, Val, Glu, Asp, or Lys,

Xaa at position 18 is Ser, Ala, Gly, Thr, Leu, Ile, Val, Glu, Asp, or Lys,

Xaa at position 19 is Tyr, Phe, Trp, Glu, Asp, or Lys,

Xaa at position 20 is Leu, Ala, Gly, Ser, Thr, Leu, Ile, Val, Glu, Asp, or Lys,

Xaa at position 21 is Glu, Asp, or Lys,

Xaa at position 22 is Gly, Ala, Ser, Thr, Leu, Ile, Val, Glu, Asp, or Lys,

Xaa at position 23 is Gln, Asn, Arg, Glu, Asp, or Lys,

Xaa at position 24 is Ala, Gly, Ser, Thr, Leu, Ile, Val, Arg, Glu, Asp, or Lys,

Xaa at position 25 is Ala, Gly, Ser, Thr, Leu, Ile, Val, Glu, Asp, or Lys,

Xaa at position 26 is Lys, Arg, Gln, Glu, Asp, or His,

Xaa at position 27 is Glu, Asp, or Lys,

Xaa at position 30 is Ala, Gly, Ser, Thr, Leu, Ile, Val, Glu, Asp, or Lys,

Xaa at position 31 is Trp, Phe, Tyr, Glu, Asp, or Lys,

Xaa at position 32 is Leu, Gly, Ala, Ser, Thr, Ile, Val, Glu, Asp, or Lys,

Xaa at position 33 is Val, Gly, Ala, Ser, Thr, Leu, Ile, Glu, Asp, or Lys,

Xaa at position 34 is Lys, Arg, Glu, Asp, or His,

Xaa at position 35 is Gly, Ala, Ser, Thr, Leu, Ile, Val, Glu, Asp, or Lys,

Xaa at position 36 is Arg, Lys, Glu, Asp, or His,

Xaa at position 37 is Gly, Ala, Ser, Thr, Leu, Ile, Val, Glu, Asp, or Lys, or is deleted, Xaa at position 38 is Arg, Lys, Glu, Asp, or His, or is deleted, Xaa at position 39 is Arg, Lys, Glu, Asp, or His, or is deleted, Xaa at position 40 is Asp, Glu, or Lys, or is deleted, Xaa at position 41 is Phe, Trp, Tyr, Glu, Asp, or Lys, or is deleted, Xaa at position 42 is Pro, Lys, Glu, or Asp, or is deleted, Xaa at position 43 is Glu, Asp, or Lys, or is deleted, Xaa at position 44 is Glu, Asp, or Lys, or is deleted, and Xaa at position 45 is Val, Glu, Asp, or Lys, or is deleted, or (a) a C-1–6-ester thereof, (b) amide, C-1–6-alkylamide, or C-1–6-dialkylamide thereof and/or (c) a pharmaceutically acceptable salt thereof, provided that (i) when the amino acid at position 37, 38, 39, 40, 41, 42, 43 or 44 is deleted, then each amino acid downstream of the amino acid is also deleted.

In a further embodiment of the GLP-1 analogue of formula II, the amino acids at positions 37–45 are absent.

In another embodiment of the GLP-1 analogue of formula II, the amino acids at positions 38–45 are absent.

In another embodiment of the GLP-1 analogue of formula II, the amino acids at positions 39–45 are absent.

In another embodiment of the GLP-1 analogue of formula II, Xaa at position 8 is Ala, Gly, Ser, Thr, Met, or Val.

In another embodiment of the GLP-1 analogue of formula II, Xaa at position 8 is Gly, Thr, Met, or Val.

In another embodiment of the GLP-1 analogue of formula II, Xaa at position 8 is Val.

In another embodiment of the GLP-1 analogue of formula II, Xaa at position 9 is Glu.

In another embodiment of the GLP-1 analogue of formula II, Xaa at position 11 is Thr.

In another embodiment of the GLP-1 analogue of formula II, Xaa at position 14 is Ser.

In another embodiment of the GLP-1 analogue of formula II, Xaa at position 16 is Val.

In another embodiment of the GLP-1 analogue of formula II, Xaa at position 17 is Ser.

In another embodiment of the GLP-1 analogue of formula II, Xaa at position 18 is Ser, Lys, Glu, or Asp.

In another embodiment of the GLP-1 analogue of formula II, Xaa at position 19 is Tyr, Lys, Glu, or Asp.

In another embodiment of the GLP-1 analogue of formula II, Xaa at position 20 is Leu, Lys, Glu, or Asp.

In another embodiment of the GLP-1 analogue of formula II, Xaa at position 21 is Glu, Lys, or Asp.

In another embodiment of the GLP-1 analogue of formula II, Xaa at position 22 is Gly, Glu, Asp, or Lys.

In another embodiment of the GLP-1 analogue of formula II, Xaa at position 23 is Gln, Glu, Asp, or Lys.

In another embodiment of the GLP-1 analogue of formula II, Xaa at position 24 is Ala, Glu, Asp, or Lys.

In another embodiment of the GLP-1 analogue of formula II, Xaa at position 25 is Ala, Glu, Asp, or Lys.

In another embodiment of the GLP-1 analogue of formula II, Xaa at position 26 is Lys, Glu, Asp, or Arg.

In another embodiment of the GLP-1 analogue of formula II, Xaa at position 27 is Glu, Asp, or Lys.

In another embodiment of the GLP-1 analogue of formula II, Xaa at position 30 is Ala, Glu, Asp, or Lys.

In another embodiment of the GLP-1 analogue of formula II, Xaa at position 31 is Trp, Glu, Asp, or Lys.

In another embodiment of the GLP-1 analogue of formula II, Xaa at position 32 is Leu, Glu, Asp, or Lys.

In another embodiment of the GLP-1 analogue of formula II, Xaa at position 33 is Val, Glu, Asp, or Lys.

In another embodiment of the GLP-1 analogue of formula II, Xaa at position 34 is Lys, Arg, Glu, or Asp.

In another embodiment of the GLP-1 analogue of formula II, Xaa at position 35 is Gly, Glu, Asp, or Lys.

In another embodiment of the GLP-1 analogue of formula II, Xaa at position 36 is Arg, Lys, Glu, or Asp.

In another embodiment of the GLP-1 analogue of formula II, Xaa at position 37 is Gly, Glu, Asp, or Lys.

In another embodiment of the GLP-1 analogue of formula II, Xaa at position 38 is Arg, or Lys, or is deleted.

In another embodiment of the GLP-1 analogue of formula II, Xaa at position 39 is deleted.

In another embodiment of the GLP-1 analogue of formula II, Xaa at position 40 is deleted.

In another embodiment of the GLP-1 analogue of formula II, Xaa at position 41 is deleted.

In another embodiment of the GLP-1 analogue of formula II, Xaa at position 42 is deleted.

In another embodiment of the GLP-1 analogue of formula II, Xaa at position 43 is deleted.

In another embodiment of the GLP-1 analogue of formula II, Xaa at position 44 is deleted.

In another embodiment of the GLP-1 analogue of formula II, Xaa at position 45 is deleted.

In another embodiment of the GLP-1 analogue of formula II, Xaa at position 26 is Arg, each of Xaa at positions 37–45 is deleted, and each of the other Xaa is the amino acid in native GLP-1(7–36).

In another embodiment of the GLP-1 analogue of formula II, Xaa at position 26 is Arg, each of Xaa at positions 38–45 is deleted, and each of the other Xaa is the amino acid in native GLP-1(7–37).

In another embodiment of the GLP-1 analogue of formula II, Xaa at position 26 is Arg, each of Xaa at positions 39–45 is deleted, and each of the other Xaa is the amino acid in native GLP-1(7–38).

In another embodiment of the GLP-1 analogue of formula II, Xaa at position 34 is Arg, each of Xaa at positions 37–45 is deleted, and each of the other Xaa is the amino acid in native GLP-1(7–36).

In another embodiment of the GLP-1 analogue of formula II, Xaa at position 34 is Arg, each of Xaa at positions 38–45 is deleted, and each of the other Xaa is the amino acid in native GLP-1(7–37).

In another embodiment of the GLP-1 analogue of formula II, Xaa at position 34 is Arg, each of Xaa at positions 39–45 is deleted, and each of the other Xaa is the amino acid in native GLP-1(7–38).

In another embodiment of the GLP-1 analogue of formula II, Xaa at positions 26 and 34 is Arg, Xaa at position 36 is Lys, each of Xaa at positions 37–45 is deleted, and each of the other Xaa is the amino acid in native GLP-1(7–36).

In another embodiment of the GLP-1 analogue of formula II, Xaa at positions 26 and 34 is Arg, Xaa at position 36 is Lys, each of Xaa at positions 38–45 is deleted, and each of the other Xaa is the amino acid in native GLP-1(7–37).

In another embodiment of the GLP-1 analogue of formula II, Xaa at positions 26 and 34 is Arg, Xaa at position 36 is Lys, each of Xaa at positions 39–45 is deleted, and each of the other Xaa is the amino acid in native GLP-1(7–38).

In another embodiment of the GLP-1 analogue of formula II, Xaa at positions 26 and 34 is Arg, Xaa at position 38 is Lys, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly, or Val, Xaa at position 37 is Glu, Xaa at position 36 is Lys, each of Xaa at positions 38–45 is deleted, and each of the other Xaa is the amino acid in native GLP-1(7–37).

In another embodiment of the GLP-1 analogue of formula II, Xaa at position 8 is Thr, Ser, Gly, or Val, Xaa at position 37 is Glu, Xaa at position 36 is Lys, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly or Val, Xaa at position 37 is Glu, Xaa at position 38 is Lys, each of Xaa at positions 39–45 is deleted, and each of the other Xaa is the amino acid in native GLP-1(7–38).

In another embodiment of the GLP-1 analogue of formula II, Xaa at position 18, 23 or 27 is Lys, and Xaa at positions 26 and 34 is Arg, each of Xaa at positions 37–45 is deleted, and each of the other Xaa is the amino acid in native GLP-1(7–36).

In another embodiment of the GLP-1 analogue of formula II, Xaa at position 18, 23 or 27 is Lys, and Xaa at positions 26 and 34 is Arg, each of Xaa at positions 38–45 is deleted, and each of the other Xaa is the amino acid in native GLP-1(7–37).

In another embodiment of the GLP-1 analogue of formula II, Xaa at position 18, 23 or 27 is Lys, and Xaa at positions 26 and 34 is Arg, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 37–45 is deleted, and each of the other Xaa is the amino acid in native GLP-1(7–36).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 38–45 is deleted, and each of the other Xaa is the amino acid in native GLP-1(7–37).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 39–45 is deleted, and each of the other Xaa is the amino acid in native GLP-1(7–38).

Such GLP-1 analogues includes, but is not limited to, $Arg^{26}$-GLP-1(7–37); $Arg^{34}$-GLP-1(7–37); $Lys^{36}$-GLP-1(7–37); $Arg^{26,34}Lys^{36}$-GLP-1(7–37); $Arg^{26,34}Lys^{38}$GLP-1(7–38); $Arg^{26,34}Lys^{39}$-GLP-1(7–39); $Arg^{26,34}Lys^{40}$-GLP-1(7–40); $Arg^{26}Lys^{36}$-GLP-1(7–37); $Arg^{34}Lys^{36}$-GLP-1(7–37); $Arg^{26}Lys^{39}$-GLP-1(7–39); $Arg^{34}Lys^{40}$-GLP-1(7–40); $Arg^{26,34}Lys^{36,39}$-GLP-1(7–39); $Arg^{26,34}Lys^{36,40}$-GLP-1(7–40); $Gly^8Arg^{26}$-GLP-1(7–37); $Gly^8Arg^{34}$-GLP-1(7–37); $Val^8$-GLP-1(7–37); $Thr^8$-GLP-1(7–37); $Gly^8$-GLP-1(7–37); $Met^8$-GLP-1(7–37); $Gly^8Lys^{36}$-GLP-1(7–37); $Gly^8Arg^{26,34}Lys^{36}$-GLP-1(7–37); $Gly^8Arg^{26,34}Lys^{39}$-GLP-1(7–39); $Gly^8Arg^{26,34}Lys^{40}$-GLP-1(7–40); $Gly^8Arg^{26}Lys^{36}$-GLP-1(7–37); $Gly^8Arg^{34}Lys^{36}$-GLP-1(7–37); $Gly^8Arg^{26}Lys^{39}$-GLP-1(7–39); $Gly^8Arg^{34}Lys^{40}$-GLP-1(7–40); $Gly^8Arg^{26,34}Lys^{36,39}$GLP-1(7–39); $Gly^8Arg^{26,34}Lys^{36,40}$GLP-1(7–40); $Arg^{26,34}Lys^{38}$GLP-1(7–38); $Arg^{26,34}Lys^{39}$GLP-1(7–39); $Arg^{26,34}Lys^{40}$GLP-1(7–40); $Arg^{26,34}Lys^{41}$GLP-1(7–41); $Arg^{26,34}Lys^{42}$GLP-1(7–42); $Arg^{26,34}Lys^{43}$GLP-1(7–43); $Arg^{26,34}Lys^{44}$GLP-1(7–44); $Arg^{26,34}Lys^{45}$GLP-1(7–45); $Arg^{26,34}Lys^{38}$GLP-1(1–38); $Arg^{26,34}Lys^{39}$GLP-1(1–39); $Arg^{26,34}Lys^{40}$GLP-1(1–40); $Arg^{26,34}Lys^{41}$GLP-1(1–41); $Arg^{26,34}Lys^{42}$GLP-1(1–42); $Arg^{26,34}Lys^{43}$GLP-1(1–43); $Arg^{26,34}Lys^{44}$GLP-1(1–44); $Arg^{26,34}Lys^{45}$GLP-1(1–45); $Arg^{26,34}Lys^{38}$GLP-1(2–38); $Arg^{26,34}Lys^{39}$GLP-1(2–39); $Arg^{26,34}Lys^{40}$GLP-1(2–40); $Arg^{26,34}Lys^{41}$GLP-1(2–41); $Arg^{26,34}Lys^{42}$GLP-1(2–42); $Arg^{26,34}Lys^{43}$GLP-1(2–43); $Arg^{26,34}Lys^{44}$GLP-1(2–44); $Arg^{26,34}Lys^{45}$GLP-1(2–45); $Arg^{26,34}Lys^{38}$GLP-1(3–38); $Arg^{26,34}Lys^{38}$GLP-1(3–38); $Arg^{26,34}Lys^{39}$GLP-1(3–39); $Arg^{26,34}Lys^{40}$GLP-1(3–40); $Arg^{26,34}Lys^{41}$GLP-1(3–41); $Arg^{26,34}Lys^{42}$GLP-1(3–42); $Arg^{26,34}Lys^{43}$GLP-1(3–43); $Arg^{26,34}Lys^{44}$GLP-1(3–44); $Arg^{26,34}Lys^{45}$GLP-1(3–45); $Arg^{26,34}Lys^{45}$GLP-1(3–45); $Arg^{26,34}Lys^{38}$GLP-1(4–38); $Arg^{26,34}Lys^{39}$GLP-1(4–39); $Arg^{26,34}Lys^{40}$GLP-1(4–40); $Arg^{26,34}Lys^{41}$GLP-1(4–41); $Arg^{26,34}Lys^{42}$GLP-1(4–42); $Arg^{26,34}Lys^{43}$GLP-1(4–43); $Arg^{26,34}Lys^{44}$GLP-1(4–44); $Arg^{26,34}Lys^{45}$GLP-1(5–45); $Arg^{26,34}Lys^{38}$GLP-1(5–38); $Arg^{26,34}Lys^{39}$GLP-1(5–39); $Arg^{26,34}Lys^{40}$GLP-1(5–40); $Arg^{26,34}Lys^{41}$GLP-1(5–41); $Arg^{26,34}Lys^{42}$GLP-1(5–42); $Arg^{26,34}Lys^{43}$GLP-1(5–43); $Arg^{26,34}Lys^{44}$GLP-1(5–44); $Arg^{26,34}Lys^{45}$GLP-1(5–45); $Arg^{26,34}Lys^{38}$GLP-1(6–38); $Arg^{26,34}Lys^{39}$GLP-1(6–39); $Arg^{26,34}Lys^{40}$GLP-1(6–40); $Arg^{26,34}Lys^{41}$GLP-1(6–41); $Arg^{26,34}Lys^{42}$GLP-1(6–42); $Arg^{26,34}Lys^{43}$GLP-1(6–43); $Arg^{26,34}Lys^{44}$GLP-1(6–44); $Arg^{26,34}Lys^{45}$GLP-1(6–45); $Arg^{26}Lys^{38}$GLP-1(1–38); $Arg^{34}Lys^{38}$GLP-1(1–38); $Arg^{26,34}Lys^{36,38}$GLP-1(1–38); $Arg^{26}Lys^{38}$GLP-1(7–38); $Arg^{34}Lys^{38}$GLP-1(7–38); $Arg^{26,34}Lys^{36,38}$GLP-1(7–38); $Arg^{26,34}Lys^{38}$GLP-1(7–38); $Arg^{26}Lys^{39}$GLP-1(1–39); $Arg^{34}Lys^{39}$GLP-1(1–39); $Arg^{26,34}Lys^{36,39}$GLP-1(1–39); $Arg^{26}Lys^{39}$GLP-1(7–39); $Arg^{34}Lys^{39}$GLP-1(7–39); and $Arg^{26,34}Lys^{36,39}$GLP-1(7–39). Each one of these specific GLP-1 constitutes an alternative embodiment of the invention.

In a still further embodiment of the invention the GLP-1 agonist is a GLP-1 derivative.

In a further embodiment of the invention the GLP-1 derivative has one or more lipophilic substituents attached to the parent peptide. The lipophilic substituents make the profile of action of the parent GLP-1 peptide more protracted, make the parent GLP-1 peptide more metabolically and physically stable, and/or increase the water solubility of the parent GLP-1 peptide.

The lipophilic substituent is characterised by having a solubility in water at 20° C. in the range from about 0.1 mg/100 ml water to about 250 mg/100 ml water, preferable in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

In a further embodiment of the invention the GLP-1 derivatives preferably have three lipophilic substituents, more preferably two lipophilic substituents, and most preferably one lipophilic substituent.

Each lipophilic substituent(s) preferably has 4–40 carbon atoms, more preferably 8–30 carbon atoms, even more preferably 8–25 carbon atoms, even more preferably 12–25 carbon atoms, and most preferably 14–18 carbon atoms.

The lipophilic substituent(s) contain a functional group which can be attached to one of the following functional groups of an amino acid of the parent GLP-1 peptide:

(a) the amino group attached to the alpha-carbon of the N-terminal amino acid, (b) the carboxy group attached to the alpha-carbon of the C-terminal amino acid, (c) the epsilon-amino group of any Lys residue, (d) the carboxy group of the R group of any Asp and Glu residue, (e) the hydroxy group of the R group of any Tyr, Ser and Thr residue, (f) the amino group of the R group of any Trp, Asn, Gln, Arg, and His residue, or (g) the thiol group of the R group of any Cys residue.

In an embodiment, a lipophilic substituent is attached to the carboxy group of the R group of any Asp and Glu residue.

In another embodiment, a lipophilic substituent is attached to the carboxy group attached to the alpha-carbon of the C-terminal amino acid.

In a most preferred embodiment, a lipophilic substituent is attached to the epsilon-amino group of any Lys residue.

Each lipophilic substituent contains a functional group which may be attached to a functional group of an amino acid of the parent GLP-1 peptide. For example, a lipophilic substituent may contain a carboxyl group which can be attached to an amino group of the parent GLP-1 peptide by means of an amide bond.

In an embodiment, the lipophilic substituent comprises a partially or completely hydrogenated cyclopentanophenathrene skeleton.

In another embodiment, the lipophilic substituent is a straight-chain or branched alkyl group.

In another embodiment, the lipophilic substituent is an acyl group of a straight-chain or branched fatty acid. Preferably, the lipophilic substituent is an acyl group having the formula $CH_3(CH_2)_nCO$—, wherein n is an integer from 4 to 38, preferably an integer from 12 to 38, and most preferably is $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— and $CH_3(CH_2)_{22}CO$—. In a more preferred embodiment, the lipophilic substituent is tetradecanoyl. In a most preferred embodiment, the lipophilic substituent is hexadecanoyl.

In another embodiment of the present invention, the lipophilic substituent has a group which is negatively charged such as a carboxylic acid group. For example, the lipophilic substituent may be an acyl group of a straight-chain or branched alkane α,ω-dicarboxylic acid of the formula HOOC(CH$_2$)$_m$CO—, wherein m is an integer from 4 to 38, preferably an integer from 12 to 38, and most preferably is HOOC(CH$_2$)$_{14}$CO—, HOOC(CH$_2$)$_{16}$CO—, HOOC(CH$_2$)$_{18}$CO—, HOOC(CH$_2$)$_{20}$CO— or HOOC(CH$_2$)$_{22}$CO—.

In a preferred embodiment of the invention, the lipophilic substituent is attached to the parent GLP-1 peptide by means of a spacer. A spacer must contain at least two functional groups, one to attach to a functional group of the lipophilic substituent and the other to a functional group of the parent GLP-1 peptide.

In an embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, preferably a dipeptide wherein the C-terminal amino acid residue is Lys, His or Trp, preferably Lys, and the N-terminal amino acid residue is Ala, Arg, Asp, Asn, Gly, Glu, Gln, Ile, Leu, Val, Phe, Pro, Ser, Tyr, Thr, Lys, His and Trp. Preferably, an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

Preferred spacers are lysyl, glutamyl, asparagyl, glycyl, beta-alanyl and gamma-aminobutanoyl, each of which constitutes an individual embodiment. Most preferred spacers are glutamyl and beta-alanyl. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a N$^ε$-acylated lysine residue.

In another embodiment, the spacer is an unbranched alkane α,ω-dicarboxylic acid group having from 1 to 7 methylene groups, which spacer forms a bridge between an amino group of the parent peptide and an amino group of the lipophilic substituent. Preferably, the spacer is succinic acid.

In a further embodiment, the lipophilic substituent with the attached spacer is a group of the formula CH$_3$(CH$_2$)$_p$NH—CO(CH$_2$)$_q$CO—, wherein p is an integer from 8 to 33, preferably from 12 to 28 and q is an integer from 1 to 6, preferably 2.

In a further embodiment, the lipophilic substituent with the attached spacer is a group of the formula CH$_3$(CH$_2$)$_r$CO—NHCH(COOH)(CH$_2$)$_2$CO—, wherein r is an integer from 4 to 24, preferably from 10 to 24.

In a further embodiment, the lipophilic substituent with the attached spacer is a group of the formula CH$_3$(CH$_2$)$_s$CO—NHCH((CH$_2$)$_2$COOH)CO—, wherein s is an integer from 4 to 24, preferably from 10 to 24.

In a further embodiment, the lipophilic substituent is a group of the formula COOH(CH$_2$)$_t$CO— wherein t is an integer from 6 to 24.

In a further embodiment, the lipophilic substituent with the attached spacer is a group of the formula —NHCH(COOH)(CH$_2$)$_4$NH—CO(CH$_2$)$_u$CH$_3$, wherein u is an integer from 8 to 18.

In a further embodiment, the lipophilic substituent with the attached spacer is a group of the formula CH$_3$(CH$_2$)$_v$CO—NH—(CH$_2$)$_z$—CO, wherein v is an integer from 4 to 24 and z is an integer from 1 to 6.

In a further embodiment, the lipophilic substituent with the attached spacer is a group of the formula —NHCH(COOH)(CH$_2$)$_4$NH—COCH((CH$_2$)$_2$COOH)NH—CO(CH$_2$)$_w$CH$_3$, wherein w is an integer from 10 to 16.

In a further embodiment, the lipophilic substituent with the attached spacer is a group of the formula —NHCH(COOH)(CH$_2$)$_4$NH—CO(CH$_2$)$_2$CH(COOH)NHCO(CH$_2$)$_x$CH$_3$, wherein x is zero or an integer from 1 to 22, preferably 10 to 16.

In a further embodiment the GLP-1 derivative is derived from a GLP-1 fragment selected from the group comprising GLP-1(7–35), GLP-1(7–36), GLP-1(7–36)amide, GLP-1(7–37), GLP-1(7–38), GLP-1(7–39), GLP-1(7–40) and GLP-1(7–41) or an analogue thereof.

In a further embodiment of the GLP-1 derivative the designation analogue comprises derivatives wherein a total of up to fifteen, preferably up to ten amino acid residues have been exchanged with any α-amino acid residue.

In a further embodiment of the GLP-1 derivative the designation analogue comprises derivatives wherein a total of up to fifteen, preferably up to ten amino acid residues have been exchanged with any α-amino acid residue which can be coded for by the genetic code.

In a further embodiment of the GLP-1 derivative the designation analogue comprises derivatives wherein a total of up to six amino acid residues have been exchanged with another α-amino acid residue which can be coded for by the genetic code.

In a further embodiment the GLP-1 derivative is a GLP-1 derivative of formula I:

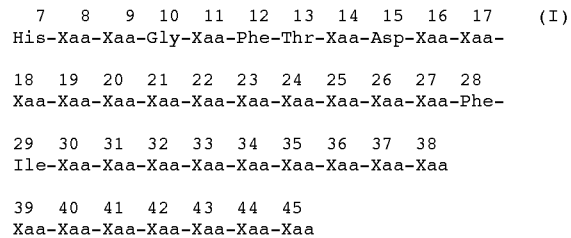

wherein
Xaa at position 8 is Ala, Gly, Ser, Thr, Leu, Ile, Val, Glu, Asp, Met, or Lys,
Xaa at position 9 is Glu, Asp, or Lys,
Xaa at position 10 is Thr, Ala, Gly, Ser, Leu, Ile, Val, Glu, Asp, or Lys,
Xaa at position 14 is Ser, Ala, Gly, Thr, Leu, Ile, Val, Glu, Asp, or Lys,
Xaa at position 16 is Val, Ala, Gly, Ser, Thr, Leu, Ile, Tyr, Glu, Asp, or Lys,
Xaa at position 17 is Ser, Ala, Gly, Thr, Leu, Ile, Val, Glu, Asp, or Lys,
Xaa at position 18 is Ser, Ala, Gly, Thr, Leu, Ile, Val, Glu, Asp, or Lys,
Xaa at position 19 is Tyr, Phe, Trp, Glu, Asp, or Lys,
Xaa at position 20 is Leu, Ala, Gly, Ser, Thr, Leu, Ile, Val, Glu, Asp, or Lys,
Xaa at position 21 is Glu, Asp, or Lys, Xaa at position 22 is Gly, Ala, Ser, Thr, Leu, Ile, Val, Glu, Asp, or Lys, Xaa at position 23 is Gln, Asn, Arg, Glu, Asp, or Lys, Xaa at position 24 is Ala, Gly, Ser, Thr, Leu, Ile, Val, Arg, Glu, Asp, or Lys, Xaa at position 25 is Ala, Gly, Ser, Thr, Leu, Ile, Val, Glu, Asp, or Lys, Xaa at position 26 is Lys, Arg, Gln, Glu, Asp, or His, Xaa at position 27 is Glu, Asp, or Lys, Xaa at position 30 is Ala, Gly, Ser, Thr, Leu, Ile, Val, Glu, Asp, or Lys, Xaa at position 31 is Trp, Phe, Tyr, Glu, Asp, or Lys, Xaa at position 32 is Leu, Gly, Ala, Ser, Thr, Ile, Val, Glu, Asp, or Lys, Xaa at position 33 is Val, Gly, Ala, Ser, Thr, Leu, Ile, Glu, Asp, or Lys, Xaa at position 34 is Lys, Arg, Glu, Asp, or His, Xaa at position 35 is Gly, Ala, Ser, Thr, Leu, Ile, Val, Glu, Asp, or Lys, Xaa at position 36 is Arg, Lys, Glu, Asp, or His, Xaa at position 37 is Gly, Ala, Ser, Thr, Leu, Ile, Val, Glu, Asp, or Lys, or is deleted, Xaa at position 38 is Arg, Lys, Glu, Asp, or His, or is deleted, Xaa at position 39 is Arg, Lys, Glu, Asp, or His, or is deleted, Xaa at position 40 is Asp, Glu, or Lys, or is deleted, Xaa at position 41 is Phe, Trp, Tyr, Glu, Asp, or Lys, or is deleted, Xaa at position 42 is Pro, Lys, Glu, or Asp, or is deleted, Xaa at position 43 is Glu, Asp, or Lys, or is deleted, Xaa at position 44 is Glu, Asp, or Lys, or is deleted, and Xaa at position 45 is Val, Glu, Asp, or Lys, or is deleted, or (a) a C-1–6-ester thereof, (b) amide, C-1–6-alkylamide, or C-1–6-dialkylamide thereof and/or (c) a pharmaceutically acceptable salt thereof, provided that
(i) when the amino acid at position 37, 38, 39, 40, 41, 42, 43 or 44 is deleted, then each amino acid downstream of the amino acid is also deleted,
(ii) the derivative of the GLP-1 analog contains only one or two Lys,
(iii) the ε-amino group of one or both Lys is substituted with a lipophilic substituent optionally via a spacer,
(iv) the total number of different amino acids between the derivative of the GLP-1 analog and the corresponding native form of GLP-1 does not exceed six.

In a further embodiment of the GLP-1 derivative of formula I, the amino acids at positions 37–45 are absent.

In another embodiment of the GLP-1 derivative of formula I, the amino acids at positions 38–45 are absent.

In another embodiment of the GLP-1 derivative of formula I, the amino acids at positions 39–45 are absent.

In another embodiment of the GLP-1 derivative of formula I, Xaa at position 8 is Ala, Gly, Ser, Thr, Leu, Ile, Val, Glu, Asp, or Lys, In another embodiment of the GLP-1 derivative of formula I, Xaa at position 8 is Ala, Gly, Ser, Thr, or Val.

In another embodiment of the GLP-1 derivative of formula I, Xaa at position 9 is Glu.

In another embodiment of the GLP-1 derivative of formula I, Xaa at position 11 is Thr.

In another embodiment of the GLP-1 derivative of formula I, Xaa at position 14 is Ser.

In another embodiment of the GLP-1 derivative of formula I, Xaa at position 16 is Val.

In another embodiment of the GLP-1 derivative of formula I, Xaa at position 17 is Ser.

In another embodiment of the GLP-1 derivative of formula I, Xaa at position 18 is Ser, Lys, Glu, or Asp.

In another embodiment of the GLP-1 derivative of formula I, Xaa at position 19 is Tyr, Lys, Glu, or Asp.

In another embodiment of the GLP-1 derivative of formula I, Xaa at position 20 is Leu, Lys, Glu, or Asp.

In another embodiment of the GLP-1 derivative of formula I, Xaa at position 21 is Glu, Lys, or Asp.

In another embodiment of the GLP-1 derivative of formula I, Xaa at position 22 is Gly, Glu, Asp, or Lys.

In another embodiment of the GLP-1 derivative of formula I, Xaa at position 23 is Gln, Glu, Asp, or Lys.

In another embodiment of the GLP-1 derivative of formula I, Xaa at position 24 is Ala, Glu, Asp, or Lys.

In another embodiment of the GLP-1 derivative of formula I, Xaa at position 25 is Ala, Glu, Asp, or Lys.

In another embodiment of the GLP-1 derivative of formula I, Xaa at position 26 is Lys, Glu, Asp, or Arg.

In another embodiment of the GLP-1 derivative of formula I, Xaa at position 27 is Glu, Asp, or Lys.

In another embodiment of the GLP-1 derivative of formula I, Xaa at position 30 is Ala, Glu, Asp, or Lys.

In another embodiment of the GLP-1 derivative of formula I, Xaa at position 31 is Trp, Glu, Asp, or Lys.

In another embodiment of the GLP-1 derivative of formula I, Xaa at position 32 is Leu, Glu, Asp, or Lys.

In another embodiment of the GLP-1 derivative of formula I, Xaa at position 33 is Val, Glu, Asp, or Lys.

In another embodiment of the GLP-1 derivative of formula I, Xaa at position 34 is Lys, Arg, Glu, or Asp.

In another embodiment of the GLP-1 derivative of formula I, Xaa at position 35 is Gly, Glu, Asp, or Lys.

In another embodiment of the GLP-1 derivative of formula I, Xaa at position 36 is Arg, Lys, Glu, or Asp.

In another embodiment of the GLP-1 derivative of formula I, Xaa at position 37 is Gly, Glu, Asp, or Lys.

In another embodiment of the GLP-1 derivative of formula I, Xaa at position 38 is Arg, or Lys, or is deleted.

In another embodiment of the GLP-1 derivative of formula I, Xaa at position 39 is deleted.

In another embodiment of the GLP-1 derivative of formula I, Xaa at position 40 is deleted.

In another embodiment of the GLP-1 derivative of formula I, Xaa at position 41 is deleted.

In another embodiment of the GLP-1 derivative of formula I, Xaa at position 42 is deleted.

In another embodiment of the GLP-1 derivative of formula I, Xaa at position 43 is deleted.

In another embodiment of the GLP-1 derivative of formula I, Xaa at position 44 is deleted.

In another embodiment of the GLP-1 derivative of formula I, Xaa at position 45 is deleted.

In another embodiment of the GLP-1 derivative of formula I, Xaa at position 26 is Arg, each of Xaa at positions 37–45 is deleted, and each of the other Xaa is the amino acid in native GLP-1(7–36).

In another embodiment of the GLP-1 derivative of formula I, Xaa at position 26 is Arg, each of Xaa at positions 38–45 is deleted, and each of the other Xaa is the amino acid in native GLP-1(7–37).

In another embodiment of the GLP-1 derivative of formula I, Xaa at position 26 is Arg, each of Xaa at positions 39–45 is deleted, and each of the other Xaa is the amino acid in native GLP-1(7–38).

In another embodiment of the GLP-1 derivative of formula I, Xaa at position 34 is Arg, each of Xaa at positions 37–45 is deleted, and each of the other Xaa is the amino acid in native GLP-1(7–36).

In another embodiment of the GLP-1 derivative of formula I, Xaa at position 34 is Arg, each of Xaa at positions 38–45 is deleted, and each of the other Xaa is the amino acid in native GLP-1(7–37).

In another embodiment of the GLP-1 derivative of formula I, Xaa at position 34 is Arg, each of Xaa at positions 39–45 is deleted, and each of the other Xaa is the amino acid in native GLP-1(7–38).

In another embodiment of the GLP-1 derivative of formula I, Xaa at positions 26 and 34 is Arg, Xaa at position 36 is Lys, each of Xaa at positions 37–45 is deleted, and each of the other Xaa is the amino acid in native GLP-1(7–36).

In another embodiment of the GLP-1 derivative of formula I, Xaa at positions 26 and 34 is Arg, Xaa at position 36 is Lys, each of Xaa at positions 38–45 is deleted, and each of the other Xaa is the amino acid in native GLP-1(7–37).

In another embodiment of the GLP-1 derivative of formula I, Xaa at positions 26 and 34 is Arg, Xaa at position 36 is Lys, each of Xaa at positions 39–45 is deleted, and each of the other Xaa is the amino acid in native GLP-1(7–38).

In another embodiment of the GLP-1 derivative of formula I, Xaa at positions 26 and 34 is Arg, Xaa at position 38 is Lys, each of Xaa at positions 39–45 is deleted, and each of the other Xaa is the amino acid in native GLP-1(7–38).

In another embodiment of the GLP-1 derivative of formula I, Xaa at position 8 is Thr, Ser, Gly or Val, Xaa at position 37 is Glu, Xaa at position 36 is Lys, each of Xaa at positions 38–45 is deleted, and each of the other Xaa is the amino acid in native GLP-1(7–37).

In another embodiment of the GLP-1 derivative of formula I, Xaa at position 8 is Thr, Ser, Gly or Val, Xaa at position 37 is Glu, Xaa at position 36 is Lys, each of Xaa at positions 39–45 is deleted, and each of the other Xaa is the amino acid in native GLP-1(7–38).

In another embodiment of the GLP-1 derivative of formula I, Xaa at position 8 is Thr, Ser, Gly or Val, Xaa at position 37 is Glu, Xaa at position 38 is Lys, each of Xaa at positions 39–45 is deleted, and each of the other Xaa is the amino acid in native GLP-1(7–38).

In another embodiment of the GLP-1 derivative of formula I, Xaa at position 18, 23 or 27 is Lys, and Xaa at positions 26 and 34 is Arg, each of Xaa at positions 37–45 is deleted, and each of the other Xaa is the amino acid in native GLP-1(7–36).

In another embodiment of the GLP-1 derivative of formula I, Xaa at position 18, 23 or 27 is Lys, and Xaa at positions 26 and 34 is Arg, each of Xaa at positions 3845 is deleted, and each of the other Xaa is the amino acid in native GLP-1(7–37).

In another embodiment of the GLP-1 derivative of formula I, Xaa at position 18, 23 or 27 is Lys, and Xaa at positions 26 and 34 is Arg, each of Xaa at positions 39–45 is deleted, and each of the other Xaa is the amino acid in native GLP-1(7–38).

In another embodiment of the GLP-1 derivative of formula I, Xaa at position 8 is Thr, Ser, Gly, or Val, Xaa at position 18, 23 or 27 is Lys, and Xaa at position 26 and 34 is Arg, each of Xaa at positions 37–45 is deleted, and each of the other Xaa is the amino acid in native GLP-1(7–36).

In another embodiment of the GLP-1 derivative of formula I, Xaa at position 8 is Thr, Ser, Gly, or Val, Xaa at position 18, 23 or 27 is Lys, and Xaa at position 26 and 34 is Arg, each of Xaa at positions 38–45 is deleted, and each of the other Xaa is the amino acid in native GLP-1(7–37).

In another embodiment of the GLP-1 derivative of formula I, Xaa at position 8 is Thr, Ser, Gly, or Val, Xaa at position 18, 23 or 27 is Lys, and Xaa at position 26 and 34 is Arg, each of Xaa at positions 39–45 is deleted, and each of the other Xaa is the amino acid in native GLP-1(7–38).

Such GLP-1 derivatives includes, but is not limited to, $Lys^{34}(N^{\epsilon}$-($\gamma$-glutamyl($N^{\alpha}$-tetradecanoyl)))GLP-1(7–37), $Arg^{26,34},Lys_8(N^{\epsilon}$-($\gamma$-glutamyl($N^{\alpha}$-hexadecanoyl)))GLP-1(7–37), $Arg^{34},Lys^{26}(N^{\epsilon}(\gamma$-glutamyl($N^{\alpha}$-dodecanoyl)))GLP-1(7–37), $Arg^{34},Lys^{26}(N^{\epsilon}(\beta$-alanyl($N^{\alpha}$-hexadecanoyl)))GLP-1(7–37), $Arg^{34},Lys^{26}(N^{\epsilon}(\alpha$-glutamyl($N^{\alpha}$-hexadecanoyl)))GLP-1(7–37), $Arg^{34},Lys^{26}(N^{\epsilon}(piperidinyl-4-carbonyl(N-hexadecanoyl)))GLP-1(7–37)$, $Arg^{34},Lys^{26}(N^{\epsilon}(\gamma$-glutamyl($N^{\alpha}$-decanoyl)))GLP-1(7–37), $Glu^{22,23,30}Arg^{26,34}Lys^{38}(N^{\epsilon}$-($\gamma$-glutamyl($N^{\alpha}$-tetradecanoyl)))-GLP-1(7–38)-OH, $Glu^{23,26}Arg^{34}Lys^{38}(N^{\epsilon}$-($\gamma$-glutamyl($N^{\alpha}$-tetradecanoyl)))-GLP-1(7–38)-OH, $Lys^{26,34}$-bis($N^{\epsilon}$-($\gamma$-glutamyl($N^{\alpha}$-tetradecanoyl)))-GLP-1(7–37)-OH, $Lys^{26,34}$-bis($N^{\epsilon}$-($\gamma$-glutamyl($N^{\alpha}$-hexadecanoyl)))-GLP-1(7–37)-OH, $Arg^{34}Lys^{26}(N^{\epsilon}$-($\gamma$-glutamyl($N^{\alpha}$-hexadecanoyl)))-GLP-1(7–37)-OH, $Arg^{26,34}Lys^{38}(N^{\epsilon}$-($\gamma$-glutamyl($N^{\alpha}$-tetradecanoyl)))-GLP-1(7–38)-OH, $Arg^{26,34}Lys^{38}(N^{\epsilon}$-($\gamma$-glutamyl($N^{\alpha}$-hexadecanoyl)))-GLP-1(7–38)-OH, $Arg^{34}Lys^{26}(N^{\epsilon}$-($\gamma$-glutamyl($N^{\alpha}$-tetradecanoyl)))-GLP-1(7–37)-OH, $Arg^{26,34}Lys^{38}(N^{\epsilon}$-($\gamma$-glutamyl($N^{\alpha}$-octadecanoyl)))-GLP-1(7–38)-OH.

$Glu^{22,23,30}Arg^{26,34}Lys^{38}(N^{\epsilon}$-($\gamma$-glutamyl($N^{\alpha}$-tetradecanoyl)))-GLP-1(7–38)-OH, $Glu^{23,26}Arg^{34}Lys^{38}(N^{\epsilon}$-($\gamma$-glutamyl($N^{\alpha}$-tetradecanoyl)))-GLP-1(7–38)-OH, $Lys^{26,34}$-bis($N^{\epsilon}$-($\omega$-carboxytridecanoyl))-GLP-1(7–37)-OH, $Lys^{26,34}$-bis($N^{\epsilon}$-($\gamma$-glutamyl($N^{\alpha}$-tetradecanoyl)))-GLP-1(7–37)-OH, $Arg^{26,34}Lys^{38}(N^{\epsilon}$-($\omega$-carboxypentadecanoyl))-GLP-1(7–38)-OH, $Lys^{26,34}$-bis($N^{\epsilon}$-($\gamma$-glutamyl($N^{\alpha}$-hexadecanoyl)))-GLP-1(7–37)-OH, $Arg^{34}Lys^{26}(N^{\epsilon}$-($\gamma$-glutamyl($N^{\alpha}$-hexadecanoyl)))-GLP-1(7–37)-OH, $Arg^{26,34}Lys^{38}(N^{\epsilon}$-($\gamma$-glutamyl($N^{\alpha}$-tetradecanoyl)))-GLP-1(7–38)-OH, $Arg^{26,34}Lys^{38}(N^{\epsilon}$-($\omega$-carboxypentadecanoyl))-GLP-1(7–38)-OH, $Arg^{26,34}Lys^{38}(N^{\epsilon}$-($\gamma$-glutamyl($N^{\alpha}$-hexadecanoyl)))-GLP-1(7–38)-OH, $Arg^{18,23,26,30,34}Lys^{38}(N^{\epsilon}$-hexadecanoyl)-GLP-1(7–38)-OH, $Arg^{26,34}Lys^{38}(N^{\epsilon}$-($\omega$-carboxytridecanoyl))-GLP-1(7–38)-OH, $Arg^{34}Lys^{26}(N^{\epsilon}$-($\gamma$-glutamyl($N^{\alpha}$-tetradecanoyl)))-GLP-1(7–37)-OH, Arg$^{26,34}$Lys$^{38}$N$^\epsilon$-(γ-glutamyl(N$^\alpha$-octadecanoyl)))-GLP-1(7–38)-OH,
Glu$^{22,23,30}$Arg$^{26,34}$Lys$^{38}$(N$^\epsilon$-(β-alanyl(N$^\alpha$-tetradecanoyl)))-GLP-1(7–38)-OH,
Glu$^{23,26}$Arg$^{34}$Lys$^{38}$(N$^\epsilon$-(β-alanyl(N$^\alpha$-tetradecanoyl)))-GLP-1(7–38)-OH,
Lys$^{26,34}$-bis(N$^\epsilon$-(β-alanyl(N$^\alpha$-tetradecanoyl)))-GLP-1(7–37)-OH,
Lys$^{26,34}$-bis(N$^\epsilon$-(β-alanyl(N$^\alpha$-hexadecanoyl)))-GLP-1(7–37)-OH,
Arg$^{34}$Lys$^{26}$(N$^\epsilon$-(β-alanyl(N$^\alpha$-hexadecanoyl)))-GLP-1(7–37)-OH,
Arg$^{26,34}$Lys$^{38}$(N$^\epsilon$-(β-alanyl(N$^\alpha$-tetradecanoyl)))-GLP-1(7–38)-OH,
Arg$^{26,34}$Lys$^{38}$(N$^\epsilon$-(β-alanyl(N$^\alpha$-hexadecanoyl)))-GLP-1(7–38)-OH,
Arg$^{34}$Lys$^{26}$(N$^\epsilon$-(β-alanyl(N$^\alpha$-tetradecanoyl)))-GLP-1(7–37)-OH,
Arg$^{26,34}$Lys$^{38}$(N$^\epsilon$-(β-alanyl(N$^\alpha$-octadecanoyl)))-GLP-1(7–38)-OH.
Glu$^{22,23,30}$Arg$^{26,34}$Lys$^{38}$(N$^\epsilon$-(β-alanyl(N$^\alpha$-tetradecanoyl)))-GLP-1(7–38)-OH,
Glu$^{23,26}$Arg$^{34}$Lys$^{38}$(N$^\epsilon$-(β-alanyl(N$^\alpha$-tetradecanoyl)))-GLP-1(7–38)-OH,
Lys$^{26,34}$-bis(N$^\epsilon$-(β-alanyl(N$^\alpha$-tetradecanoyl)))-GLP-1(7–37)-OH,
Lys$^{26,34}$-bis(N$^\epsilon$-(β-alanyl(N$^\alpha$-hexadecanoyl)))-GLP-1(7–37)-OH,
Arg$^{34}$Lys$^{26}$(N$^\epsilon$-(β-alanyl(N$^\alpha$-hexadecanoyl)))-GLP-1(7–37)-OH,
Arg$^{26,34}$Lys$^{38}$(N$^\epsilon$-(β-alanyl(N$^\alpha$-tetradecanoyl)))-GLP-1(7–38)-OH,
Arg$^{26,34}$Lys$^{38}$(N$^\epsilon$-(β-alanyl(N$^\alpha$-hexadecanoyl)))-GLP-1(7–38)-OH,
Arg$^{34}$Lys$^{26}$(N$^\epsilon$-(β-alanyl(N$^\alpha$-tetradecanoyl)))-GLP-1(7–38)-OH,
Arg$^{26,34}$Lys$^{38}$(N$^\epsilon$-(β-alanyl(N$^\alpha$-hexadecanoyl)))-GLP-1(7–38)-OH,
Lys$^{26}$(N$^\epsilon$-tetradecanoyl)))-GLP-1(7–37);
Lys$^{34}$(N$^\epsilon$-tetradecanoyl)))-GLP-1(7–37);
Lys$^{26,34}$(N$^\epsilon$-tetradecanoyl)))-GLP-1(7–37);
Gly$^8$Lys$^{26}$(N$^\epsilon$-tetradecanoyl)))-GLP-1(7–37);
Gly$^8$Lys$^{34}$(N$^\epsilon$-tetradecanoyl)))-GLP-1(7–37);
Gly$^8$Lys$^{26,34}$-bis(N$^\epsilon$-tetradecanoyl)))-GLP-1(7–37);
Val$^8$Lys$^{26}$(N$^\epsilon$-tetradecanoyl)-GLP-1(7–37);
Val$^8$Lys$^{34}$(N$^\epsilon$-tetradecanoyl)-GLP-1(7–37);
Val$^8$Lys$^{26,34}$-bis(N$^\epsilon$-tetradecanoyl)-GLP-1(7–37);
Arg$^{26}$Lys$^{34}$(N$^\epsilon$-tetradecanoyl)-GLP-1(7–37);
Lys$^{26}$(N$^\epsilon$-tetradecanoyl)-GLP-1(7–38);
Lys$^{34}$(N$^\epsilon$-tetradecanoyl)-GLP-1(7–38);
Lys$^{26,34}$-bis(N$^\epsilon$-tetradecanoyl)-GLP-1(7–38);
Gly$^8$Lys$^{26}$(N$^\epsilon$-tetradecanoyl)-GLP-1(7–38);
Gly$^8$Lys$^{34}$(N$^\epsilon$-tetradecanoyl)-GLP-1(7–38);
Gly$^8$Lys$^{26,34}$-bis(N$^\epsilon$-tetradecanoyl)-GLP-1(7–38);
Arg$^{26}$Lys$^{34}$(N$^\epsilon$-tetradecanoyl)-GLP-1(7–38);
Lys$^{26}$(N$^\epsilon$-tetradecanoyl)-GLP-1(7–39);
Lys$^{34}$(N$^\epsilon$-tetradecanoyl)-GLP-1(7–39);
Lys$^{26,34}$-bis(N$^\epsilon$-tetradecanoyl)-GLP-1(7–39);
Gly$^8$Lys$^{26}$(N$^\epsilon$-tetradecanoyl)-GLP-1(7–39);
Gly$^8$Lys$^{34}$(N$^\epsilon$-tetradecanoyl)-GLP-1(7–39);
Gly$^8$Lys$^{26,34}$-bis(N$^\epsilon$-tetradecanoyl)-GLP-1(7–39);
Arg$^{26}$Lys$^{34}$(N$^\epsilon$-tetradecanoyl)-GLP-1(7–39);
Lys$^{26}$(N$^\epsilon$-tetradecanoyl)-GLP-1(7–40);
Lys$^{34}$(N$^\epsilon$-tetradecanoyl)-GLP-1(7–40);
Lys$^{26,34}$-bis(N$^\epsilon$-tetradecanoyl)-GLP-1(7–40);
Gly$^8$Lys$^{26}$(N$^\epsilon$-tetradecanoyl)-GLP-1(7–40);
Gly$^8$Lys$^{34}$(N$^\epsilon$-tetradecanoyl)-GLP-1(7–40);
Gly$^8$Lys$^{26,34}$-bis(N$^\epsilon$-tetradecanoyl)-GLP-1(7–40);
Arg$^{26}$Lys$^{34}$(N$^\epsilon$-tetradecanoyl)-GLP-1(7–40);
Lys$^{26}$(N$^\epsilon$-tetradecanoyl)-GLP-1(7–36);
Lys$^{34}$(N$^\epsilon$-tetradecanoyl)-GLP-1(7–36);
Lys$^{26,34}$-bis(N$^\epsilon$-tetradecanoyl)GLP-1(7–36);
Gly$^8$Lys$^{26}$(N$^\epsilon$-tetradecanoyl)-GLP-1(7–36);
Gly$^8$Lys$^{34}$(N$^\epsilon$-tetradecanoyl)-GLP-1(7–36);
Gly$^8$Lys$^{26,34}$-bis(N$^\epsilon$-tetradecanoyl)-GLP-1(7–36);
Arg$^{26}$Lys$^{34}$(N$^\epsilon$-tetradecanoyl)-GLP-1(7–36);
Lys$^{26}$(N$^\epsilon$-tetradecanoyl)-GLP-1(7–35);
Lys$^{34}$(N$^\epsilon$-tetradecanoyl)-GLP-1(7–35);
Lys$^{26,34}$-bis(N$^\epsilon$-tetradecanoyl)-GLP-1(7–35);
Gly$^8$Lys$^{26}$(N$^\epsilon$-tetradecanoyl)-GLP-1(7–35);
Gly$^8$Lys$^{34}$(N$^\epsilon$-tetradecanoyl)-GLP-1(7–35);
Gly$^8$Lys$^{26,34}$-bis(N$^\epsilon$-tetradecanoyl)-GLP-1(7–35);
Arg$^{26}$Lys$^{34}$(N$^\epsilon$-tetradecanoyl)-GLP-1(7–35);
Lys$^{26}$(N$^\epsilon$-tetradecanoyl)-GLP-1(7–36)amide;
Lys$^{34}$(N$^\epsilon$-tetradecanoyl)-GLP-1(7–36)amide;
Lys$^{26,34}$-bis(N$^\epsilon$-tetradecanoyl)-GLP-1(7–36)amide;
Gly$^8$Lys$^{26}$(N$^\epsilon$-tetradecanoyl)-GLP-1(7–36)amide;
Gly$^8$Lys$^{34}$(N$^\epsilon$-tetradecanoyl)-GLP-1(7–36)amide;
Gly$^8$Lys$^{26,34}$-bis(N$^\epsilon$-tetradecanoyl)-GLP-1(7–36)amide;
Arg$^{26}$Lys$^{34}$(N$^\epsilon$-tetradecanoyl)-GLP-1(7–36)amide;
Gly$^8$Arg$^{26}$Lys$^{34}$(N$^\epsilon$-tetradecanoyl)-GLP-1(7–37);
Lys$^{26}$(N$^\epsilon$-tetradecanoyl)Arg$^{34}$-GLP-1(7–37);
Gly$^8$Lys$^{26}$(N$^\epsilon$-tetradecanoyl)Arg$^{34}$-GLP-1(7–37);
Arg$^{26,34}$Lys$^{36}$(N$^\epsilon$-tetradecanoyl)-GLP-1(7–37);
Gly$^8$Arg$^{26,34}$Lys$^{36}$(N$^\epsilon$-tetradecanoyl)-GLP-1(7–37);
Gly$^8$Arg$^{26}$Lys$^{34}$(N$^\epsilon$-tetradecanoyl)-GLP-1(7–38);
Lys$^{26}$(N$^\epsilon$-tetradecanoyl)Arg$^{34}$-GLP-1(7–38);
Gly$^8$L$^{26}$(N$^\epsilon$-tetradecanoyl)Arg-GLP-1(7–38);
Arg$^{26,34}$Lys$^{36}$(N$^\epsilon$-tetradecanoyl)-GLP-1(7–38);
Arg$^{26,34}$Lys$^{38}$(N$^\epsilon$-tetradecanoyl)-GLP-1(7–38);
Gly$^8$Arg$^{26,34}$Lys$^{36}$(N$^\epsilon$-tetradecanoyl)-GLP-1(7–38);
Gly$^8$Arg$^{26}$Lys$^{34}$(N$^\epsilon$-tetradecanoyl)-GLP-1(7–39);
Lys$^{26}$(N$^\epsilon$-tetradecatnoyl(N$^\epsilon$)Arg$^{34}$-GLP-1(7–39);
Gly$^8$Lys$^{26}$(N$^\epsilon$-tetradecanoyl)Arg$^{34}$-GLP-1(7–39);
Arg$^{26,34}$Lys$^{36}$(N$^\epsilon$-tetradecanoyl)-GLP-1(7–39);
Gly$^8$Arg$^{26,34}$Lys$^{36}$(N$^\epsilon$-tetradecanoyl)-GLP-1(7–39);
Gly$^8$Arg$^{26}$Lys$^{34}$(N$^\epsilon$-tetradecanoyl)-GLP-1(7–40);
Lys$^{26}$(N$^\epsilon$-tetradecanoyl)Arg$^{34}$-GLP-1(7–40);
Gly$^8$Lys$^{26}$(N$^\epsilon$-tetradecanoyl)Arg$^{34}$-GLP-1(7–40);
Arg$^{26,34}$Lys$^{36}$(N$^\epsilon$-tetradecanoyl)-GLP-1(7–40);
Gly$^8$Arg$^{26,34}$Lys$^{36}$(N$^\epsilon$-tetradecanoyl)-GLP-1(7–40);
Lys$^{26}$(N$^\epsilon$-(ω-carboxynonadecanoyl))-GLP-1(7–37);
Lys$^{34}$(N$^\epsilon$-(ω-carboxynonadecanoyl))-GLP-1(7–37);
Lys$^{26,34}$-bis(N$^\epsilon$-(ω-carboxynonadecanoyl))-GLP-1(7–37);
Gly$^8$Lys$^{26}$(N$^\epsilon$-(ω-carboxynonadecanoyl))-GLP-1(7–37);
Gly$^8$Lys$^{34}$(N$^\epsilon$-(ω-carboxynonadecanoyl))-GLP-1(7–37);

Gly$^8$Lys$^{26,34}$-bis(N$^\epsilon$-($\omega$-carboxynonadecanoyl))-GLP-1(7–37);
Lys$^{26}$(N$^\epsilon$-($\omega$-carboxynonadecanoyl))-GLP-1(7–38);
Lys$^{34}$(N$^\epsilon$-($\omega$-carboxynonadecanoyl))-GLP-1(7–38);
Lys$^{26,34}$-bis(N$^\epsilon$-($\omega$-carboxynonadecanoyl))-GLP-1(7–38);
Gly$^8$Lys$^{26}$(N$^\epsilon$-($\omega$-carboxynonadecanoyl))-GLP-1(7–38);
Gly$^8$Lys$^{34}$(N$^\epsilon$-($\omega$-carboxynonadecanoyl))-GLP-1(7–38);
Gly$^8$Lys$^{26,34}$-bis(N$^\epsilon$-($\omega$-carboxynonadecanoyl))-GLP-1(7–38);
Lys$^{26}$(N$^\epsilon$-($\omega$-carboxynonadecanoyl))-GLP-1(7–39);
Lys$^{34}$(N$^\epsilon$-($\omega$-carboxynonadecanoyl))-GLP-1(7–39);
Lys$^{26,34}$-bis(N$^\epsilon$-($\omega$-carboxynonadecanoyl))-GLP-1(7–39);
Gly$^8$Lys$^{26}$(N$^\epsilon$-($\omega$-carboxynonadecanoyl))-GLP-1(7–39);
Gly$^8$Lys$^{34}$(N$^\epsilon$-($\omega$-carboxynonadecanoyl))-GLP-1(7–39);
Gly$^8$Lys$^{26,34}$-bis(N$^\epsilon$-($\omega$-carboxynonadecanoyl))-GLP-1(7–39);
Lys$^{26}$(N$^\epsilon$-($\omega$-carboxynonadecanoyl))-GLP-1(7–40);
Lys$^{34}$(N$^\epsilon$-($\omega$-carboxynonadecanoyl))-GLP-1(7–40);
Lys$^{26,34}$-bis(N$^\epsilon$($\omega$-carboxynonadecanoyl))-GLP-1(7–40);
Gly$^8$Lys$^{26}$(N$^\epsilon$-($\omega$-carboxynonadecanoyl))-GLP-1(7–40);
Gly$^8$Lys$^{34}$(N$^\epsilon$-($\omega$-carboxynonadecanoyl)-GLP-1(7–40);
Gly$^8$Lys$^{26,34}$-(N$^\epsilon$-($\omega$-carboxynonadecanoyl))-GLP-1(7–40);
Lys$^{26}$(N$^\epsilon$-($\omega$-carboxynonadecanoyl))-GLP-1(7–36);
Lys$^{34}$(N$^\epsilon$-($\omega$-carboxynonadecanoyl))-GLP-1(7–36);
Lys$^{26,34}$-bis(N$^\epsilon$-($\omega$-carboxynonadecanoyl))-GLP-1(7–36);
Gly$^8$Lys$^{26}$(N$^\epsilon$-($\omega$-carboxynonadecanoyl))-GLP-1(7–36);
Gly$^8$Lys$^{34}$(N$^\epsilon$-($\omega$-carboxynonadecanoyl))-GLP-1(7–36);
Gly$^8$Lys$^{26,34}$-bis(N$^\epsilon$-($\omega$-carboxynonadecanoyl))-GLP-1(7–36);
Lys$^{26}$(N$^\epsilon$-($\omega$-carboxynonadecanoyl))-GLP-1(7–36)amide;
Lys$^{34}$(N$^\epsilon$-($\omega$-carboxynonadecanoyl))-GLP-1(7–36)amide;
Lys$^{26,34}$-bis(N$^\epsilon$-($\omega$-carboxynonadecanoyl))-GLP-1(7–36)amide;
Gly$^8$Lys$^{26}$(N$^\epsilon$-($\omega$-carboxynonadecanoyl))-GLP-1(7–36)amide;
Gly$^8$Lys$^{34}$(N$^\epsilon$-($\omega$-carboxynonadecanoyl))-GLP-1(7–36)amide;
Gly$^8$Lys$^{26,34}$-bis(N$^\epsilon$-($\omega$-carboxynonadecanoyl))-GLP-1(7–36)amide;
Lys$^{26}$(N$^\epsilon$-($\omega$-carboxynonadecanoyl))-GLP-1(7–35);
Lys$^{34}$(N$^\epsilon$-($\omega$-carboxynonadecanoyl))-GLP-1(7–35);
Lys$^{26,34}$-bis(N$^\epsilon$-($\omega$-carboxynonadecanoyl))-GLP-1(7–35);
Gly$^8$Lys$^{26}$(N$^\epsilon$-($\omega$-carboxynonadecanoyl))-GLP-1(7–35);
Gly$^8$Lys$^{34}$(N$^\epsilon$-($\omega$-carboxynonadecanoyl))-GLP-1(7–35);
Gly$^8$Lys$^{26,34}$-bis(N$^\epsilon$-($\omega$-carboxynonadecanoyl))-GLP-1(7–35);
Arg$^{26}$Lys$^{34}$(N$^\epsilon$-($\omega$-carboxynonadecanoyl))-GLP-1(7–37);
Gly$^8$Arg$^{26}$Lys$^{34}$(N$^\epsilon$-($\omega$-carboxynonadecanoyl))-GLP-1(7–37);
Lys$^{26}$(N$^\epsilon$-($\omega$-carboxynonadecanoyl))Arg$^{34}$-GLP-1(7–37);
Gly$^8$Lys$^{26}$(N$^\epsilon$-($\omega$-carboxynonadecanoyl))Arg$^{34}$-GLP-1(7–37);
Arg$^{26,34}$Lys$^{36}$(N$^\epsilon$-($\omega$-carboxynonadecanoyl))-GLP-1(7–37);
Gly$^8$Arg$^{26,34}$Lys$^{36}$(N$^\epsilon$-($\omega$-carboxynonadecanoyl))-GLP-1(7–37);
Arg$^{26}$Lys$^{34}$(N$^\epsilon$-($\omega$-carboxynonadecanoyl))-GLP-1(7–38);
Gly$^8$Arg$^{26}$Lys$^{34}$(N$^\epsilon$-($\omega$-carboxynonadecanoyl))-GLP-1(7–38);
Lys$^{26}$(N$^\epsilon$-($\omega$-carboxynonadecanoyl))Arg$^{34}$-GLP-1(7–38);
Gly$^8$Lys$^{26}$(N$^\epsilon$-($\omega$-carboxynonadecanoyl))Arg$^{34}$-GLP-1(7–38);
Arg$^{26,34}$Lys$^{36}$(N$^\epsilon$-($\omega$-carboxynonadecanoyl))-GLP-1(7–38);
Arg$^{26,34}$Lys$^{38}$(N$^\epsilon$-($\omega$-carboxynonadecanoyl))-GLP-1(7–38);
Gly$^8$Arg$^{26,34}$Lys$^{36}$(N$^\epsilon$-($\omega$-carboxynonadecanoyl))-GLP-1(7–38);
Arg$^{26}$Lys$^{34}$(N$^\epsilon$-($\omega$-carboxynonadecanoyl))-GLP-1(7–39);
Gly$^8$Arg$^{26}$Lys$^{34}$(N$^\epsilon$-($\omega$-carboxynonadecanoyl))-GLP-1(7–39);
Lys$^{26}$(N$^\epsilon$-($\omega$-carboxynonadecanoyl))Arg$^{34}$-GLP-1(7–39);
Gly$^8$Lys$^{26}$(N$^\epsilon$-($\omega$-carboxynonadecanoyl))Arg$^{34}$-GLP-1(7–39);
Arg$^{26,34}$Lys$^{36}$(N$^\epsilon$-($\omega$-carboxynonadecanoyl))-GLP-1(7–39);
Gly$^8$Arg$^{26,34}$Lys$^{36}$(N$^\epsilon$-($\omega$-carboxynonadecanoyl))-GLP-1(7–39);
Arg$^{26}$Lys$^{34}$(N$^\epsilon$-($\omega$-carboxynonadecanoyl))-GLP-1(7–40);
Gly$^8$Arg$^{26}$Lys$^{34}$(N$^\epsilon$-($\omega$-carboxynonadecanoyl))-GLP-1(7–40);
Lys$^{26}$(N$^\epsilon$-($\omega$-carboxynonadecanoyl))Arg$^{34}$-GLP-1(7–40);
Gly$^8$L$^{26}$(N$^\epsilon$-($\omega$-carboxynonadecanoyl))Arg$^{34}$-GLP-1(7–40);
Arg$^{26,34}$Lys$^{36}$(N$^\epsilon$-($\omega$-carboxynonadecanoyl))-GLP-1(7–40);
Gly$^8$Arg$^{26,34}$Lys$^{36}$(N$^\epsilon$-($\omega$-carboxynonadecanoyl))-GLP-1(7–40);
Lys$^{26}$(N$^\epsilon$-(7-deoxycholoyl))-GLP-1(7–37);
Lys$^{34}$(N$^\epsilon$-(7-deoxycholoyl))-GLP-1(7–37);
Lys$^{26,34}$-bis(N$^\epsilon$-(7-deoxycholoyl))-GLP-1(7–37);
Gly$^8$Lys$^{26}$(N$^\epsilon$-(7-deoxycholoyl))-GLP-1(7–37);
Gly$^8$Lys$^{34}$(N$^\epsilon$-(7-deoxycholoyl))-GLP-1(7–37);
GlyLys$^{26,34}$-bis(N$^\epsilon$-(7-deoxycholoyl))-GLP-1(7–37);
Arg$^{26}$Lys$^{34}$(N$^\epsilon$-(7-deoxycholoyl))-GLP-1(7–37);
Lys$^{26}$(N$^\epsilon$-(7-deoxycholoyl))-GLP-1(7–38);
Lys$^{34}$(N$^\epsilon$-(7-deoxycholoyl))-GLP-1(7–38);
Lys$^{26,34}$-bis(N$^\epsilon$-(7-deoxycholoyl))-GLP-1(7–38);
Gly$^8$(N$^\epsilon$-(7-deoxycholoyl))-GLP-1(7–38);
Gly$^8$Lys$^{34}$(N$^\epsilon$-(7-deoxycholoyl))-GLP-1(7–38);
Gly$^8$Lys$^{26,34}$-bis(N$^\epsilon$-(7-deoxycholoyl))-GLP-1(7–38);
Arg$^{26}$Lys$^{34}$(N$^\epsilon$-(7-deoxycholoyl))-GLP-1(7–38);
Lys$^{26}$(N$^\epsilon$-(7-deoxycholoyl))-GLP-1(7–39);
Lys$^{34}$(N$^\epsilon$-(7-deoxycholoyl))-GLP-1(7–39);
Lys$^{26,34}$-bis(N$^\epsilon$-(7-deoxycholoyl))-GLP-1(7–39);
Gly$^8$Lys$^{26}$(N$^\epsilon$-(7-deoxycholoyl))-GLP-1(7–39);

Gly$^8$Lys$^{34}$(N$^\epsilon$-(7-deoxycholoyl))-GLP-1(7–39);
Gly$^8$Lys$^{26,34}$-bis(N$^\epsilon$-(7-deoxycholoyl))-GLP-1(7–39);
Arg$^{26}$Lys$^{34}$(N$^\epsilon$-(7-deoxycholoyl))-GLP-1(7–39);
Lys$^{26}$(N$^\epsilon$-(7-deoxycholoyl))-GLP-1(7–40);
Lys$^{34}$(N$^\epsilon$-(7-deoxycholoyl))-GLP-1(7–40);
Lys$^{26,34}$-bis(N$^\epsilon$-(7-deoxycholoyl))-GLP-1(7–40);
Gly$^8$Lys$^{26}$(N$^\epsilon$-(7-deoxycholoyl))-GLP-1(7–40);
Gly$^8$Lys$^{34}$(N$^\epsilon$-(7-deoxycholoyl))-GLP-1(7–40);
Gly$^8$Lys$^{26,34}$-bis(N$^\epsilon$-(7-deoxycholoyl))-GLP-1(7–40);
Arg$^{26}$Lys$^{34}$(N$^\epsilon$-(7-deoxycholoyl))-GLP-1(7–40);
Lys$^{26}$(N$^\epsilon$-(7-deoxycholoyl))-GLP-1(7–36);
Lys$^{34}$(N$^\epsilon$-(7-deoxycholoyl))-GLP-1(7–36);
Lys$^{26,34}$-bis(N$^\epsilon$-(7-deoxycholoyl))-GLP-1(7–36);
Gly$^8$Lys$^{26}$(N$^\epsilon$-(7-deoxycholoyl))-GLP-1(7–36);
Gly$^8$Lys$^{34}$(N$^\epsilon$-(7-deoxycholoyl))-GLP-1(7–36);
Gly$^8$Lys$^{26,34}$-bis(N$^\epsilon$-(7-deoxycholoyl))-GLP-1(7–36);
Arg$^{26}$Lys$^{34}$(N$^\epsilon$-(7-deoxycholoyl))-GLP-1(7–36);
Lys$^{26}$(N$^\epsilon$-(7-deoxycholoyl))-GLP-1(7–35);
Lys$^{34}$(N$^\epsilon$-(7-deoxycholoyl))-GLP-1(7–35);
Lys$^{26,34}$-bis(N$^\epsilon$-(7-deoxycholoyl))-GLP-1(7–35);
Gly$^8$Lys$^{26}$(N$^\epsilon$-(7-deoxycholoyl))-GLP-1(7–35);
Gly$^8$Lys$^{34}$(N$^\epsilon$-(7-deoxycholoyl))-GLP-1(7–35);
Gly$^8$Lys$^{26,34}$-bis(N$^\epsilon$-(7-deoxycholoyl))-GLP-1(7–35);
Arg$^{26}$Lys$^{34}$(N$^\epsilon$-(7-deoxycholoyl))-GLP-1(7–35);
Lys$^{26}$(N$^\epsilon$-(7-deoxycholoyl))-GLP-1(7–36)amide;
Lys$^{34}$(N$^\epsilon$-(7-deoxycholoyl))-GLP-1(7–36)amide;
Lys$^{26,34}$-bis(N$^\epsilon$-(7-deoxycholoyl))-GLP-1(7–36)amide;
Gly$^8$Lys$^{26}$(N$^\epsilon$-(7-deoxycholoyl))-GLP-1(7–36)amide;
Gly$^8$Lys$^{34}$(N$^\epsilon$-(7-deoxycholoyl))-GLP-1(7–36)amide;
Gly$^8$Lys$^{26,34}$(N$^\epsilon$-(7-deoxycholoyl))-GLP-1(7–36)amide;
Arg$^{26}$Lys$^{34}$(N$^\epsilon$-(7-deoxycholoyl))-GLP-1(7–36)amide;
Gly$^8$Arg$^{26}$Lys$^{34}$(N$^\epsilon$-(7-deoxycholoyl))-GLP-1(7–367);
Lys$^{26}$(N$^\epsilon$-(7-deoxycholoyl))Arg$^{34}$-GLP-1(7–37)amide;
Gly$^8$Lys$^{26}$(N$^\epsilon$-(7-deoxycholoyl))Arg$^{34}$-GLP-1(7–37);
Arg$^{26,34}$Lys$^{36}$(N$^\epsilon$-(7-deoxycholoyl))-GLP-1(7–37);
Gly$^8$Arg$^{26,34}$Lys$^{36}$(N$^\epsilon$-(7-deoxycholoyl))-GLP-1(7–37);
Lys$^{26}$(N$^\epsilon$-(choloyl))-GLP-1(7–37);
Lys$^{34}$(N$^\epsilon$-(choloyl))-GLP-1(7–37);
Lys$^{26,34}$-bis(N$^\epsilon$-(choloyl))-GLP-1(7–37);
Gly$^8$Lys$^{26}$(N$^\epsilon$-(choloyl))-GLP-1(7–37);
Gly$^8$Lys$^{34}$(N$^\epsilon$-(choloyl))-GLP-1(7–37);
Gly$^8$Lys$^{26,34}$-bis(N$^\epsilon$-(choloyl))-GLP-1(7–37);
Arg$^{26}$Lys$^{34}$(N$^\epsilon$-(choloyl))-GLP-1(7–37);
Gly$^8$Arg$^{26}$Lys$^{34}$(N$^\epsilon$-(7-deoxycholoyl))-GLP-1(7–38);
Lys$^{26}$(N$^\epsilon$-(7-deoxycholoyl))Arg$^{34}$-GLP-1(7–38);
Gly$^8$Lys$^{26}$(N$^\epsilon$-(7-deoxycholoyl))Arg$^{34}$-GLP-1(7–38);
Arg$^{26,34}$Lys$^{36}$(N$^\epsilon$-(7-deoxycholoyl))-GLP-1(7–38);
Arg$^{26,34}$Lys$^{38}$(N$^\epsilon$-(7-deoxycholoyl))-GLP-1(7–38);
Gly$^8$Arg$^{26,34}$Lys$^{36}$(N$^\epsilon$-(7-deoxycholoyl))-GLP-1(7–38);
Lys$^{26}$(N$^\epsilon$-(choloyl))-GLP-1(7–38);
Lys$^{34}$(N$^\epsilon$-(choloyl))-GLP-1(7–38);
Lys$^{26,34}$-bis(N$^\epsilon$-(choloyl))-GLP-1(7–38);
Gly$^8$Lys$^{26}$(N$^\epsilon$-(choloyl))-GLP-1(7–38);
Gly$^8$Lys$^{34}$(N$^\epsilon$-(choloyl))-GLP-1(7–38);
Gly$^8$Lys$^{26,34}$-bis(N$^\epsilon$-(choloyl))-GLP-1(7–38);
Arg$^{26}$Lys$^{34}$(N$^\epsilon$-(choloyl))-GLP-1(7–38);
Gly$^8$Arg$^{26}$Lys$^{34}$(N$^\epsilon$-(7-deoxycholoyl))-GLP-1(7–39);
Lys$^{26}$(N$^\epsilon$-(7-deoxycholoyl))Arg$^{34}$-GLP-1(7–39);
Gly$^8$Lys$^{26}$(N$^\epsilon$-(7-deoxycholoyl))Arg$^{34}$-GLP-1(7–39);
Arg$^{26,34}$Lys$^{36}$(N$^\epsilon$-(7-deoxycholoyl))-GLP-1(7–39);
Gly$^8$Arg$^{26,34}$Lys$^{36}$(N$^\epsilon$-(7-deoxycholoyl))-GLP-1(7–39);
Lys$^{26}$(N$^\epsilon$-(choloyl))-GLP-1(7–39);
Lys$^{34}$(N$^\epsilon$-(choloyl))-GLP-1(7–39);
Lys$^{26,34}$-bis(N$^\epsilon$-(choloyl))-GLP-1(7–39);
Gly$^8$Lys$^{26}$(N$^\epsilon$-(choloyl))-GLP-1(7–39);
Gly$^8$Lys$^{34}$(N$^\epsilon$-(choloyl))-GLP-1(7–39);
Gly$^8$Lys$^{26,34}$-bis(N$^\epsilon$-(choloyl))-GLP-1(7–39);
Arg$^{26}$Lys$^{34}$(N$^\epsilon$-(choloyl))-GLP-1(7–39);
Gly$^8$Arg$^{26}$Lys$^{34}$(N$^\epsilon$-(7-deoxycholoyl))-GLP-1(7–40);
Lys$^{26}$(N$^\epsilon$-(7-deoxycholoyl))Arg$^{34}$-GLP-1(7–40);
Gly$^8$Lys$^{26}$(N$^\epsilon$-(7-deoxycholoyl))Arg$^{34}$-GLP-1(7–40);
Arg$^{26,34}$Lys$^{36}$(N$^\epsilon$-(7-deoxycholoyl))-GLP-1(7–40);
Gly$^8$Arg$^{26,34}$Lys$^{36}$(N$^\epsilon$-(7-deoxycholoyl))-GLP-1(7–40);
Lys$^{26}$(N$^\epsilon$-(choloyl))-GLP-1(7–40);
Lys$^{34}$(N$^\epsilon$-(choloyl))-GLP-1(7–40);
Lys$^{26,34}$-bis(N$^\epsilon$-(choloyl))-GLP-1(7–40);
Gly$^8$Lys$^{26}$(N$^\epsilon$-(choloyl))-GLP-1(7–40);
Gly$^8$Lys$^{34}$(N$^\epsilon$-(choloyl))-GLP-1(7–40);
Gly$^8$Lys$^{26,34}$-bis(N$^\epsilon$-(choloyl))-GLP-1(7–40);
Arg$^{26}$Lys$^{34}$(N$^\epsilon$-(choloyl))-GLP-1(7–40);
Lys$^{26}$(N$^\epsilon$-(choloyl))-GLP-1(7–36);
Lys$^{34}$(N$^\epsilon$-(choloyl))-GLP-1(7–36);
Lys$^{26,34}$(N$^\epsilon$-(choloyl))-GLP-1(7–36);
Gly$^8$Lys$^{26}$(N$^\epsilon$-(choloyl))-GLP-1(7–36);
Gly$^8$Lys$^{34}$(N$^\epsilon$-(choloyl))-GLP-1(7–36);
Gly$^8$Lys$^{26,34}$-bis(N$^\epsilon$-(choloyl))-GLP-1(7–36);
Arg$^{26}$Lys$^{34}$(N$^\epsilon$-(choloyl))-GLP-1(7–36);.
Lys$^{26}$(N$^\epsilon$-(choloyl))-GLP-1(7–35);
Lys$^{34}$(N$^\epsilon$-(choloyl))-GLP-1(7–35);
Lys$^{26,34}$-bis(N$^\epsilon$-(choloyl))-GLP-1(7–35);
Gly$^8$Lys$^{26}$(N$^\epsilon$-(choloyl))-GLP-1(7–35);
Gly$^8$Lys$^{34}$(N$^\epsilon$-(choloyl))-GLP-1(7–35);
Gly$^8$Lys$^{26,34}$-bis(N$^\epsilon$-(choloyl))-GLP-1(7–35);
Arg$^{26}$Lys$^{34}$(N$^\epsilon$-(choloyl))-GLP-1(7–35);
Lys$^{26}$(N$^\epsilon$-(choloyl))-GLP-1(7–36)amide;
Lys$^{34}$(N$^\epsilon$-(choloyl))-GLP-1(7–36)amide;
Lys$^{26,34}$-bis(N$^\epsilon$-(choloyl))-GLP-1(7–36)amide;
Gly$^8$Lys$^{26}$(N$^\epsilon$-(choloyl))-GLP-1(7–36)amide;
Gly$^8$Lys$^{34}$(N$^\epsilon$-(choloyl))-GLP-1(7–36)amide;
Gly$^8$Lys$^{26,34}$-bis(N$^\epsilon$-(choloyl))-GLP-1(7–36)amide;
Arg$^{26}$Lys$^{34}$(N$^\epsilon$-(choloyl))-GLP-1(7–36)amide;
Gly$^8$Arg$^{26}$Lys$^{34}$(N$^\epsilon$-(choloyl))-GLP-1(7–37);
Lys$^{26}$(N$^\epsilon$-(choloyl))Arg$^{34}$-GLP-1(7–37);
Gly$^8$Lys$^{26}$(N$^\epsilon$-(choloyl))Arg$^{34}$-GLP-1(7–37);
Arg$^{26,34}$Lys$^{36}$(N$^\epsilon$-(choloyl))-GLP-1(7–37);
Gly$^8$Arg$^{26,34}$Lys$^{36}$(N$^\epsilon$-(choloyl))-GLP-1(7–37);
Lys$^{26}$(N$^\epsilon$-(lithocholoyl))-GLP-1(7–37);
Lys$^{34}$(N$^\epsilon$-(lithocholoyl))-GLP-1(7–37);
Lys$^{26,34}$-bis(N$^\epsilon$-(lithocholoyl))-GLP-1(7–37);
Gly$^8$Lys$^{26}$(N$^\epsilon$-(lithocholoyl))-GLP-1(7–37);
Gly$^8$Lys$^{34}$(N$^\epsilon$-(lithocholoyl))-GLP-1(7–37);
Gly$^8$Lys$^{26,34}$-bis(N$^\epsilon$-(lithocholoyl))-GLP-1(7–37);
Arg$^{26}$Lys$^{34}$(N$^\epsilon$-(lithocholoyl))-GLP-1(7–37);

Gly⁸Arg²⁶Lys³⁴(Nᵉ-(choloyl))-GLP-1(7–38);
Lys²⁶(Nᵉ-(choloyl))Arg³⁴-GLP-1(7–38);
Gly⁸Lys²⁶(Nᵉ-(choloyl))Arg³⁴-GLP-1(7–38);
Arg²⁶,³⁴Lys³⁶(Nᵉ-(choloyl))-GLP-1(7–38);
Arg²⁶,³⁴Lys³⁸(Nᵉ-(choloyl))-GLP-1(7–38);
Gly⁸Arg²⁶,³⁴Lys³⁶(Nᵉ-(choloyl))-GLP-1(7–38);
Lys²⁶(Nᵉ-(lithocholoyl))-GLP-1(7–38);
Lys³⁴(Nᵉ-(lithocholoyl))-GLP-1(7–38);
Lys²⁶,³⁴-bis(Nᵉ-(lithocholoyl))-GLP-1(7–38);
Gly⁸Lys²⁶(Nᵉ-(lithocholoyl))-GLP-1(7–38);
Gly⁸Lys³⁴(Nᵉ-(lithocholoyl))-GLP-1(7–38);
Gly⁸Lys²⁶,³⁴-bis(Nᵉ-(lithocholoyl))-GLP-1(7–38);
Arg²⁶Lys³⁴(Nᵉ-(lithocholoyl))-GLP-1(7–38);
Gly⁸Arg²⁶Lys³⁴(Nᵉ-(choloyl))-GLP-1(7–39);
Lys²⁶(Nᵉ-(choloyl))Arg³⁴-GLP-1(7–39);
Gly⁸Lys²⁶(Nᵉ-(choloyl))Arg³⁴-GLP-1(7–39);
Arg²⁶,³⁴Lys³⁶(Nᵉ-(choloyl))-GLP-1(7–39);
Gly⁸Arg²⁶,³⁴Lys³⁶(Nᵉ-(choloyl))-GLP-1(7–39);
Lys²⁶(Nᵉ-(lithocholoyl))-GLP-1(7–39);
Lys³⁴(Nᵉ-(lithocholoyl))-GLP-1(7–39);
Lys²⁶,³⁴-bis(Nᵉ-(lithocholoyl))-GLP-1(7–39);
Gly⁸Lys²⁶(Nᵉ-(lithocholoyl))-GLP-1(7–39);
Gly⁸Lys³⁴(Nᵉ-(lithocholoyl))-GLP-1(7–39);
Gly⁸Lys²⁶,³⁴-bis(Nᵉ-(lithocholoyl))-GLP-1(7–39);
Arg²⁶Lys³⁴(Nᵉ-(lithocholoyl))-GLP-1(7–39);
Gly⁸Arg²⁶Lys³⁴(Nᵉ-(choloyl))-GLP-1(7–40);
Lys²⁶(Nᵉ-(choloyl))Arg³⁴-GLP-14(7–40);
Gly⁸Lys²⁶(Nᵉ-(choloyl))Arg³⁴-GLP-1(7–40);
Arg²⁶,³⁴Lys³⁶(Nᵉ-(choloyl))-GLP-1(7–40);
Gly⁸Arg²⁶,³⁴Lys³⁶(Nᵉ-(choloyl))-GLP-1(7–40);
Lys²⁶(Nᵉ-(lithocholoyl))-GLP-1(7–40);
Lys³⁴(Nᵉ-(lithocholoyl))-GLP-1(7–40);
Lys²⁶,³⁴-bis(Nᵉ-(lithocholoyl))-GLP-1(7–40);
Gly⁸Lys²⁶(Nᵉ-(lithocholoyl))-GLP-1(7–40);
Gly⁸Lys³⁴(Nᵉ-(lithocholoyl))-GLP-1(7–40);
Gly⁸Lys²⁶,³⁴-bis(Nᵉ-(lithocholoyl))-GLP-1(7–40);
Arg²⁶Lys³⁴(Nᵉ-(lithocholoyl))-GLP-1(7–37);
Lys²⁶(Nᵉ-(lithocholoyl))-GLP-1(7–36);
Lys³⁴(Nᵉ-(lithocholoyl))-GLP-1(7–36);
Lys²⁶,³⁴-bis(Nᵉ-(lithocholoyl))-GLP-1(7–36);
Gly⁸Lys²⁶(Nᵉ-(lithocholoyl))-GLP-1(7–36);
Gly⁸Lys³⁴(Nᵉ-(lithocholoyl))-GLP-1(7–36);
Gly⁸Lys²⁶,³⁴-bis(Nᵉ-(lithocholoyl))-GLP-1(7–36);
Arg²⁶Lys³⁴(Nᵉ-(lithocholoyl))-GLP-1(7–36);
Lys²⁶(Nᵉ-(lithocholoyl))-GLP-1(7–35);
Lys³⁴(Nᵉ-(lithocholoyl))-GLP-1(7–35);
Lys²⁶,³⁴-bis(Nᵉ-(lithocholoyl))-GLP-1(7–35);
Gly⁸Lys²⁶(Nᵉ-(lithocholoyl))-GLP-1(7–35);
Gly⁸Lys³⁴(Nᵉ-(lithocholoyl))-GLP-1(7–35);
Gly⁸Lys²⁶,³⁴-bis(Nᵉ-(lithocholoyl))-GLP-1(7–35);
Arg²⁶Lys³⁴(Nᵉ-(lithocholoyl))-GLP-1(7–35);
Lys²⁶(Nᵉ-(lithocholoyl))-GLP-1(7–36)amide;
Lys³⁴(Nᵉ-(lithocholoyl))-GLP-1(7–36)amide;
Lys²⁶,³⁴-bis(Nᵉ-(lithocholoyl))-GLP-1(7–36)amide;
Gly⁸Lys²⁶(Nᵉ-(lithocholoyl))-GLP-1(7–36)amide;
Gly⁸Lys³⁴(Nᵉ-(lithocholoyl))-GLP-1(7–36)amide;
Gly⁸Lys²⁶,³⁴-bis(Nᵉ-(lithocholoyl))-GLP-1(7–36)amide;
Arg²⁶Lys³⁴(Nᵉ-(lithocholoyl))-GLP-1(7–36)amide;
Gly⁸Arg²⁶Lys³⁴(Nᵉ-(lithocholoyl))-GLP-1(7–37);
Lys²⁶(Nᵉ-(lithocholoyl))Arg³⁴-GLP-1(7–37);
Gly⁸Lys²⁶(Nᵉ-(lithocholoyl))Arg³⁴-GLP-1(7–37);
Arg²⁶,³⁴Lys³⁶(Nᵉ-(lithocholoyl))-GLP-1(7–37);
Arg²⁶,³⁴Lys³⁸(Nᵉ-(lithocholoyl))-GLP-1(7–37);
Gly⁸Arg²⁶,³⁴Lys³⁶(Nᵉ-(lithocholoyl))-GLP-1(7–37);
Gly⁸Arg²⁶Lys³⁴(Nᵉ-(lithocholoyl))-GLP-1(7–38);
Lys²⁶(Nᵉ-(lithocholoyl))Arg³⁴-GLP-1(7–38);
Gly⁸Lys²⁶(Nᵉ-(lithocholoyl))-GLP-1(7–38);
Arg²⁶,³⁴Lys³⁶(Nᵉ-(lithocholoyl))-GLP-1(7–38);
Arg²⁶,³⁴Lys³⁸(Nᵉ-(lithocholoyl))-GLP-1(7–38);
Gly⁸Arg²⁶,³⁴Lys³⁶(Nᵉ-(lithocholoyl))-GLP-1(7–38);
Gly⁸Arg²⁶Lys³⁴(Nᵉ-(lithocholoyl))-GLP-1(7–39);
Lys²⁶(Nᵉ-(lithocholoyl))Arg³⁴-GLP-1(7–39);
Gly⁸Lys²⁶(Nᵉ-(lithocholoyl))Arg³⁴-GLP-1(7–39);
Arg²⁶,³⁴Lys³⁶(Nᵉ-(lithocholoyl))-GLP-1(7–39);
Gly⁸Arg²⁶,³⁴Lys³⁶(Nᵉ-(lithocholoyl))-GLP-1(7–39);
Gly⁸Arg²⁶Lys³⁴(Nᵉ-(lithocholoyl))-GLP-1(7–40);
Lys²⁶(Nᵉ-(lithocholoyl))Arg³⁴-GLP-1(7–40);
Gly⁸Lys²⁶(Nᵉ-(lithocholoyl))Arg³⁴-GLP-1(7–40);
Arg²⁶,³⁴Lys³⁶(Nᵉ-(lithocholoyl))-GLP-1(7–40) and
Gly⁸Arg²⁶,³⁴Lys³⁶(Nᵉ-(lithocholoyl))-GLP-1(7–40).

Each one of these specific GLP-1 derivatives constitutes an alternative embodiment of the invention.

The most preferred GLP-1 derivative is Arg³⁴, Lys²⁶(Nᵉ-(γ-Glu(Nᵅ-hexadecanoyl)))-GLP-1(7–37).

In a further embodiment of the GLP-1 derivative, a parent peptide for a derivative of the invention is Arg²⁶-GLP-1 (7–37); Arg³⁴-GLP-1(7–37); Lys³⁶-GLP-1(7–37); Arg²⁶,³⁴Lys³⁶-GLP-1(7–37); Arg²⁶,³⁴Lys³⁸GLP-1(7–38); Arg²⁶,³⁴Lys³⁹-GLP-1(7–39); Arg²⁶,³⁴Lys⁴⁰-GLP-1(7–40); Arg²⁶Lys³⁶-GLP-1(7–37); Arg³⁴Lys³⁶-GLP-1(7–37); Arg²⁶Lys³⁹-GLP-1(7–39); Arg³⁴Lys⁴⁰-GLP-1(7–40); Arg²⁶,³⁴Lys³⁶,³⁹-GLP-1(7–39); Arg²⁶,³⁴Lys³⁶,⁴⁰-GLP-1(7–40); Gly⁸Arg²⁶-GLP-1(7–37); Gly⁸Arg³⁴-GLP-1(7–37); Gly⁸Lys³⁶-GLP-1(7–37); Gly⁸Arg²⁶,³⁴Lys³⁶-GLP-1(7–37); Gly⁸Arg²⁶,³⁴Lys³⁹-GLP-1(7–39); Gly⁸Arg²⁶,³⁴Lys⁴⁰-GLP-1(7–40); Gly⁸Arg²⁶Lys³⁶-GLP-1(7–37); Gly⁸Arg³⁴Lys³⁶-GLP-1(7–37); Gly⁸Arg²⁶Lys³⁹-GLP-1(7–39); Gly⁸Arg³⁴Lys⁴⁰-GLP-1(7–40); Gly⁸Arg²⁶,³⁴Lys³⁶,³⁹-GLP-1(7–39); Gly⁸Arg²⁶,³⁴Lys³⁶,⁴⁰-GLP-1(7–40); Val⁸Arg²⁶-GLP-1(7–37); Val⁸Arg³⁴-GLP-1(7–37); Val⁸Lys³⁶-GLP-1(7–37); Val⁸Arg²⁶,³⁴Lys³⁶-GLP-1(7–37); Val⁸Arg²⁶,³⁴Lys³⁹-GLP-1(7–39); Val⁸Arg²⁶,³⁴Lys⁴⁰-GLP-1(7–40); Val⁸Arg²⁶Lys³⁶-GLP-1(7–37); Val⁸Arg³⁴Lys³⁶-GLP-1(7–37); Val⁸Arg²⁶Lys³⁹-GLP-1(7–39); Val⁸Arg³⁴Lys⁴⁰-GLP-1(7–40); Val⁸Arg²⁶,³⁴Lys³⁶,³⁹-GLP-1(7–39); or Val⁸Arg²⁶,³⁴Lys³⁶,⁴⁰-GLP-1(7–40).

In a further embodiment of the GLP-1 derivative, a parent peptide for a derivative of the invention is: Arg²⁶,³⁴Lys³⁸GLP-1(7–38); Arg²⁶,³⁴Lys³⁹GLP-1(7–39); Arg²⁶,³⁴Lys⁴⁰GLP-1(7–40); Arg²⁶,³⁴Lys⁴¹GLP-1(7–41); Arg²⁶,³⁴Lys⁴²GLP-1(7–42); Arg²⁶,³⁴Lys⁴³GLP-1(7–43); Arg²⁶,³⁴Lys⁴⁴GLP-1(7–44); Arg²⁶,³⁴Lys⁴⁵GLP-1(7–45); Arg²⁶Lys³⁸GLP-1(7–38); Arg³⁴Lys³⁸GLP-1(7–38); Arg²⁶,³⁴Lys³⁶,³⁸GLP-1(7–38); Arg²⁶,³⁴Lys³⁸GLP-1(7–38); Arg²⁶Lys³⁹GLP-1(7–39); Arg³⁴Lys³⁹GLP-1(1–39); Arg²⁶,³⁴Lys³⁶,³⁹GLP-1(1–39); Arg²⁶Lys³⁹GLP-1(7–39); Arg³⁴Lys³⁹GLP-1(7–39); Arg²⁶,³⁴Lys³⁶,³⁹GLP-1(7–39).

In a further embodiment of the GLP-1 derivative, the parent peptide is selected from the group comprising Arg²⁶-

GLP-1(7–37), Arg$^{34}$-GLP-1(7–37), Lys$^{36}$-GLP-1(7–37); Arg$^{26,34}$Lys$^{36}$-GLP-1(7–37), Arg$^{26}$Lys$^{36}$-GLP-1(7–37), Arg$^{34}$Lys$^{36}$-GLP-1(7–37), Gly$^8$Arg$^{26}$-GLP-1(7–37), Gly$^8$Arg$^{34}$-GLP-1(7–37), Gly$^8$Lys$^{36}$-GLP-1(7–37), Gly$^8$Arg$^{26,34}$Lys$^{36}$-GLP-1(7–37), Gly$^8$Arg$^{26}$Lys$^{36}$-GLP-1(7–37) and Gly$^8$Arg$^{34}$Lys$^{36}$-GLP-1(7–37).

In a further embodiment of the GLP-1 derivative, the parent peptide is selected from the group comprising Arg$^{26}$Lys$^{38}$-GLP-1(7–38), Arg$^{26,34}$Lys$^{38}$-GLP-1(7–38), Arg$^{26,34}$Lys$^{36,38}$-GLP-1(7–38), Gly$^8$Arg$^{26}$Lys$^{38}$-GLP-1(7–38) and Gly$^8$Arg$^{26,34}$Lys$^{36,38}$-GLP-1(7–38).

In a further embodiment of the GLP-1 derivative, the parent peptide is selected from the group comprising Arg$^{26}$Lys$^{39}$-GLP-1(7–39), Arg$^{26,34}$Lys$^{36,39}$-GLP-1(7–39), Gly$^8$Arg$^{26}$Lys$^{39}$-GLP-1(7–39), and Gly$^8$Arg$^{26,34}$Lys$^{36,39}$-GLP-1(7–39).

In a further embodiment of the GLP-1 derivative, the parent peptide is selected from the group comprising Arg$^{34}$Lys$^{40}$-GLP-1(7–40), Arg$^{26,34}$Lys$^{36,40}$-GLP-1(7–40), Gly$^8$Arg$^{34}$Lys$^{40}$-GLP-1(7–40) and Gly$^8$Arg$^{26,34}$Lys$^{36,40}$-GLP-1(7–40).

In a further embodiment of the GLP-1 derivative, the parent peptide is: Arg$^{26}$-GLP-1(7–36); Arg$^{34}$-GLP-1(7–36); Arg$^{26,34}$Lys$^{36}$-GLP-1(7–36); Arg$^{26}$-GLP-1(7–36)amide; Arg$^{34}$-GLP-1(7–36)amide; Arg$^{26,34}$Lys$^{36}$-GLP-1(7–36)amide; Arg$^{26}$-GLP-1(7–37); Arg$^{34}$-GLP-1(7–37); Arg$^{26,34}$Lys$^{36}$-GLP-1(7–37); Arg$^{26}$-GLP-1(7–38); Arg$^{34}$-GLP-1(7–38); Arg$^{26,34}$Lys$^{38}$GLP-1(7–38); Arg$^{26}$-GLP-1(7–39); Arg$^{34}$-GLP-1(7–39); Arg$^{26,34}$Lys$^{39}$GLP-1(7–39); Gly$^8$Arg$^{26}$-GLP-1(7–36); Gly$^8$Arg$^{34}$-GLP-1(7–36); Gly$^8$Arg$^{26,34}$Lys$^{36}$-GLP-1(7–36); Gly$^8$Arg$^{26}$-GLP-1(7–36)amide; Gly$^8$Arg$^{34}$-GLP-1(7–36)amide; Gly$^8$Arg$^{26,34}$Lys$^{36}$-GLP-1(7–36)amide; Gly$^8$Arg$^{26}$-GLP-1(7–37); Gly$^8$Arg$^{34}$-GLP-1(7–37); Gly$^8$Arg$^{26,34}$Lys$^{36}$-GLP-1(7–37); Gly$^8$Arg$^{26}$-GLP-1(7–38); Gly$^8$Arg$^{34}$-GLP-1(7–38); Gly$^8$Arg$^{26,34}$Lys$^{38}$GLP-1(7–38); Gly$^8$Arg$^{26}$-GLP-1(7–39); Gly$^8$Arg$^{34}$-GLP-1(7–39); Gly$^8$Arg$^{26,34}$Lys$^{39}$-GLP-1(7–39); Val$^8$Arg$^{26}$-GLP-1(7–36); Val$^8$Arg$^{34}$-GLP-1(7–36); Val$^8$Arg$^{26,34}$Lys$^{36}$-GLP-1(7–36); Val$^8$Arg$^{26}$-GLP-1(7–36)amide; Val$^8$Arg$^{34}$-GLP-1(7–36)amide; Val$^8$Arg$^{26,34}$Lys$^{36}$-GLP-1(7–36)amide; Val$^8$Arg$^{26}$-GLP-1(7–37); Val$^8$Arg$^{34}$-GLP-1(7–37); Val$^8$Arg$^{26,34}$Lys$^{36}$-GLP-1(7–37)amide; Val$^8$Arg$^{26}$-GLP-1(7–38); Val$^8$Arg$^{34}$-GLP-1(7–38); Val$^8$Arg$^{26,34}$Lys$^{38}$GLP-1(7–38); Val$^8$Arg$^{26}$-GLP-1(7–39); Val$^8$Arg$^{34}$-GLP-1(7–39); Val$^8$Arg$^{26,34}$Lys$^{39}$-GLP-1(7–39); Ser$^8$Arg$^{26}$-GLP-1(7–36); Ser$^8$Arg$^{34}$-GLP-1(7–36); Ser$^8$Arg$^{26,34}$Lys$^{36}$-GLP-1(7–36); Ser$^8$Arg$^{26}$-GLP-1(7–36)amide; Ser$^8$Arg$^{34}$-GLP-1(7–36)amide; Ser$^8$Arg$^{26,34}$Lys$^{36}$-GLP-1(7–36)amide; Ser$^8$Arg$^{26}$-GLP-1(7–37); Ser$^8$Arg$^{34}$-GLP-1(7–37); Ser$^8$Arg$^{26,34}$Lys$^{36}$-GLP-1(7–37); Ser$^8$Arg$^{26}$-GLP-1(7–38); Ser$^8$Arg$^{34}$-GLP-1(7–38); Ser$^8$Arg$^{26,34}$Lys$^{38}$GLP-1(7–38); Ser$^8$Arg$^{26}$-GLP-1(7–39); Ser$^8$Arg$^{34}$-GLP-1(7–39); Ser$^8$Arg$^{26,34}$Lys$^{39}$-GLP-1(7–39); Thr$^8$Arg$^{26}$-GLP-1(7–36); Thr$^8$Arg$^{34}$-GLP-1(7–36); Thr$^8$Arg$^{26,34}$Lys$^{36}$-GLP-1(7–36); Thr$^8$Arg$^{26}$-GLP-1(7–36)amide; Thr$^8$Arg$^{34}$-GLP-1(7–36)amide; Thr$^8$Arg$^{26,34}$Lys$^{36}$-GLP-1(7–36)amide; Thr$^8$Arg$^{26}$-GLP-1(7–37); Thr$^8$Arg$^{34}$-GLP-1(7–37); Thr$^8$Arg$^{26,34}$Lys$^{36}$-GLP-1(7–37); Thr$^8$Arg$^{26}$-GLP-1(7–38); Thr$^8$Arg$^{34}$-GLP-1(7–38); Thr$^8$Arg$^{26,34}$Lys$^{38}$GLP-1(7–38); Thr$^8$Arg$^{26}$-GLP-1(7–39); Thr$^8$Arg$^{34}$-GLP-1(7–39); Thr$^8$Arg$^{26,34}$Lys$^{39}$-GLP-1(7–39); Val$^8$Glu$^{35}$Arg$^{26,34}$Lys$^{36}$-GLP-1(7–36); Val$^8$Glu$^{35}$Arg$^{26,34}$Lys$^{36}$-GLP-1(7–36)amide; Val$^8$Glu$^{36}$Arg$^{26,34}$Lys$^{37}$GLP-1(7–37); Val$^8$Glu$^{37}$Arg$^{26,34}$Lys$^{38}$GLP-1(7–38); Val$^8$Glu$^{38}$Arg$^{26,34}$Lys$^{39}$-GLP-1(7–39); Val$^8$Glu$^{38}$Arg$^{26,34}$Lys$^{36}$-GLP-1(7–36); Val$^8$Glu$^{35}$Arg$^{26,34}$Lys$^{36}$-GLP-1(7–36)amide; Val$^8$Glu$^{36}$Arg$^{26,34}$Lys$^{37}$GLP-1(7–37); Val$^8$Glu$^{37}$Arg$^{26,34}$Lys$^{38}$GLP-1(7–38); Val$^8$Glu$^{38}$Arg$^{26,34}$Lys$^{39}$-GLP-1(7–39); Val$^8$Asp$^{35}$Arg$^{26,34}$Lys$^{36}$-GLP-1(7–36); Val$^8$Asp$^{35}$Arg$^{26,34}$Lys$^{36}$-GLP-1(7–36)amide; Val$^8$Asp$^{36}$Arg$^{26,34}$Lys$^{37}$GLP-1(7–37); Val$^8$Asp$^{37}$Arg$^{26,34}$Lys$^{38}$GLP-1(7–38); Val$^8$Asp$^{38}$Arg$^{26,34}$Lys$^{39}$-GLP-1(7–39); Val$^8$Asp$^{35}$Arg$^{26,34}$Lys$^{36}$-GLP-1(7–36); Val$^8$Asp$^{35}$Arg$^{26,34}$Lys$^{36}$-GLP-1(7–36)amide; Val$^8$Asp$^{36}$Arg$^{26,34}$Lys$^{37}$GLP-1(7–37); Val$^8$Asp$^{37}$Arg$^{26,34}$Lys$^{38}$GLP-1(7–38); Val$^8$Asp$^{38}$Arg$^{26,34}$Lys$^{39}$-GLP-1(7–39); Ser$^8$Glu$^{35}$Arg$^{26,34}$Lys$^{36}$-GLP-1(7–36); Ser$^8$Glu$^{35}$Arg$^{26,34}$Lys$^{36}$-GLP-1(7–36)amide; Ser$^8$Glu$^{36}$Arg$^{26,34}$Lys$^{37}$GLP-1(7–37); Ser$^8$Glu$^{37}$Arg$^{26,34}$Lys$^{38}$GLP-1(7–38); Ser$^8$Glu$^{38}$Arg$^{26,34}$Lys$^{39}$-GLP-1(7–39); Ser$^8$Glu$^{35}$Arg$^{26,34}$Lys$^{36}$-GLP-1(7–36); Ser$^8$Glu$^{35}$Arg$^{26,34}$Lys$^{36}$-GLP-1(7–36)amide; Ser$^8$Glu$^{36}$Arg$^{26,34}$Lys$^{37}$GLP-1(7–37); Ser$^8$Glu$^{37}$Arg$^{26,34}$Lys$^{38}$GLP-1(7–38); Ser$^8$Glu$^{38}$Arg$^{26,34}$Lys$^{39}$-GLP-1(7–39); Ser$^8$Asp$^{35}$Arg$^{26,34}$Lys$^{36}$-GLP-1(7–36); Ser$^8$Asp$^{35}$Arg$^{26,34}$Lys$^{36}$-GLP-1(7–36)amide; Ser$^8$Asp$^{36}$Arg$^{26,34}$Lys$^{37}$GLP-1(7–37); Ser$^8$Asp$^{37}$Arg$^{26,34}$Lys$^{38}$GLP-1(7–38); Ser$^8$Asp$^{38}$Arg$^{26,34}$Lys$^{39}$-GLP-1(7–39); Ser$^8$Asp$^{35}$Arg$^{26,34}$Lys$^{36}$-GLP-1(7–36); Ser$^8$Asp$^{35}$Arg$^{26,34}$Lys$^{36}$-GLP-1(7–36)amide; Ser$^8$Asp$^{36}$Arg$^{26,34}$Lys$^{37}$GLP-1(7–37); Ser$^8$Asp$^{37}$Arg$^{26,34}$Lys$^{38}$GLP-1(7–38); Ser$^8$Asp$^{38}$Arg$^{26,34}$Lys$^{39}$-GLP-1(7–39); Thr$^8$Glu$^{35}$Arg$^{26,34}$Lys$^{36}$-GLP-1(7–36); Thr$^8$Glu$^{35}$Arg$^{26,34}$Lys$^{37}$-GLP-1(7–36)amide; Thr$^8$Glu$^{36}$Arg$^{26,34}$Lys$^{37}$GLP-1(7–37); Thr$^8$Glu$^{37}$Arg$^{26,34}$Lys$^{38}$GLP-1(7–38); Thr$^8$Glu$^{38}$Arg$^{26,34}$Lys$^{39}$-GLP-1(7–39); Thr$^8$Glu$^{35}$Arg$^{26,34}$Lys$^{36}$-GLP-1(7–36); Thr$^8$Glu$^{35}$Arg$^{26,34}$Lys$^{36}$-GLP-1(7–36)amide; Thr$^8$Glu$^{36}$Arg$^{26,34}$Lys$^{37}$GLP-1(7–37); Thr$^8$Glu$^{37}$Arg$^{26,34}$Lys$^{38}$GLP-1(7–38); Thr$^8$Glu$^{38}$Arg$^{26,34}$Lys$^{39}$-GLP-1(7–39); Thr$^8$Asp$^{35}$Arg$^{26,34}$Lys$^{36}$-GLP-1(7–36); Thr$^8$Asp$^{35}$Arg$^{26,34}$Lys$^{36}$-GLP-1(7–36)amide; Thr$^8$Asp$^{36}$Arg$^{26,34}$Lys$^{37}$GLP-1(7–37); Thr$^8$Asp$^{37}$Arg$^{26,34}$Lys$^{38}$GLP-1(7–38); Thr$^8$Asp$^{38}$Arg$^{26,34}$Lys$^{39}$-GLP-1(7–39); Thr$^8$Asp$^{35}$Arg$^{26,34}$Lys$^{36}$-GLP-1(7–36); Thr$^8$Asp$^{35}$Arg$^{26,34}$Lys$^{36}$-GLP-1(7–36)amide; Thr$^8$Asp$^{36}$Arg$^{26,34}$Lys$^{37}$GLP-1(7–37); Thr$^8$Asp$^{37}$Arg$^{26,34}$Lys$^{38}$GLP-1(7–38); Thr$^8$Asp$^{38}$Arg$^{26,34}$Lys$^{39}$-GLP-1(7–39); Gly$^8$Glu$^{35}$Arg$^{26,34}$Lys$^{36}$-GLP-1(7–36); Gly$^8$Glu$^{35}$Arg$^{26,34}$Lys$^{36}$-GLP-1(7–36)amide; Gly$^8$Glu$^{36}$Arg$^{26,34}$Lys$^{37}$GLP-1(7–37); Gly$^8$Glu$^{37}$Arg$^{26,34}$Lys$^{38}$GLP1(7–38); Gly$^8$Glu$^{38}$Arg$^{26,34}$Lys$^{39}$-GLP-1(7–39); Gly$^8$Glu$^{35}$Arg$^{26,34}$Lys$^{36}$-GLP-1(7–36); Gly$^8$Glu$^{35}$Arg$^{26,34}$Lys$^{36}$-GLP-1(7–36)amide; Gly$^8$Glu$^{36}$Arg$^{26,34}$Lys$^{37}$GLP-1(7–37); Gly$^8$Glu$^{37}$Arg$^{26,34}$Lys$^{38}$GLP-1(7–38); Gly$^8$Glu$^{38}$Arg$^{26,34}$Lys$^{39}$-GLP-1(7–39); Gly$^8$Asp$^{35}$Arg$^{26,34}$Lys$^{36}$-GLP-1(7–36); Gly$^8$Asp$^{35}$Arg$^{26,34}$Lys$^{36}$GLP-1(7–36)amide; Gly$^8$Asp$^{36}$Arg$^{26,34}$Lys$^{37}$GLP-1(7–37); Gly$^8$Asp$^{37}$Arg$^{26,34}$Lys$^{38}$GLP-1(7–38); Gly$^8$Asp$^{38}$Arg$^{26,34}$Lys$^{39}$GLP-1(7–39); Gly$^8$Asp$^{35}$Arg$^{26,34}$Lys$^{36}$-GLP-1(7–36); Gly$^8$Asp$^{35}$Arg$^{26,34}$Lys$^{36}$-GLP-1(7–36)amide; Gly$^8$Asp$^{36}$Arg$^{26,34}$Lys$^{37}$GLP(7–37); Gly$^8$Asp$^{37}$Arg$^{26,34}$Lys$^{38}$GLP-1(7–38); Gly$^8$Asp$^{38}$Arg$^{26,34}$Lys$^{39}$-GLP-1(7–39); Arg$^{26,34}$Lys$^{18}$-GLP-1(7–36); Arg$^{26,34}$Lys$^{18}$-GLP-1(7–36)amide; Arg$^{26,34}$Lys$^{18}$GLP-1(7–37); Arg$^{26,34}$Lys$^{18}$GLP-12(7–38); Gly$^8$Asp$^{19}$Arg$^{26,34}$Lys$^{18}$-GLP-1(7–36); Gly$^8$Asp$^{17}$Arg$^{26,34}$Lys$^{18}$-GLP-1(7–36); Gly$^8$Asp$^{19}$Arg$^{26,34}$Lys$^{18}$-GLP-1(7–36)amide; Gly$^8$Asp$^{17}$Arg$^{26,34}$Lys$^{18}$-GLP-1(7–36)amide; Gly$^8$Asp$^{19}$Arg$^{26,34}$Lys$^{18}$GLP-1(7–37); Gly$^8$Asp$^{19}$Arg$^{26,34}$Lys$^{18}$-GLP-1(7–38); Gly$^8$Asp$^{17}$Arg$^{26,34}$Lys$^{18}$-GLP-1(7–38); Arg$^{26,34}$Lys$^{23}$-GLP-1(7–36); Arg$^{26,34}$Lys$^{23}$-GLP-1(7–36)amide; Arg$^{26,34}$Lys$^{23}$GLP-1(7–37); Arg$^{26,34}$Lys$^{23}$GLP-1(7–38); Gly$^8$Asp$^{24}$Arg$^{26,34}$Lys$^{23}$-GLP-1(7–36); Gly$^8$Asp$^{22}$Arg$^{26,34}$Lys$^{23}$-GLP-1(7–36); Gly$^8$Asp$^{24}$Arg$^{26,34}$Lys$^{23}$-GLP-1(7–36)amide; Gly$^8$Asp$^{22}$Arg$^{26,34}$Lys$^{23}$-GLP-1(7–36)amide; Gly$^8$Asp$^{24}$Arg$^{26,34}$Lys$^{23}$GLP-1(7–37); Gly$^8$Asp$^{24}$Arg$^{26,34}$Lys$^{23}$GLP-1(7–38); Gly$^8$Asp$^{22}$Arg$^{26,34}$Lys$^{23}$GLP-1(7–38); Arg$^{26,34}$Lys$^{27}$-GLP-1(7–36); Arg$^{26,34}$ Lys$^{27}$-GLP-1(7–36)amide; Arg$^{26,34}$Lys$^{27}$GLP-1(7–37); Arg$^{26,34}$Lys$^{27}$GLP-1(7–38); Gly$^8$Asp$^{28}$Arg$^{26,34}$Lys$^{27}$-GLP-1(7–36); Gly$^8$Asp$^{26}$Arg$^{26,34}$Lys$^{27}$-GLP-1(7–36); Gly$^8$Asp$^{28}$Arg$^{26,34}$Lys$^{27}$-GLP-1(7–36)amide; Gly$^8$Asp$^{26}$Arg$^{26,34}$Lys$^{27}$-GLP-1(7–36)amide; Gly$^8$Asp$^{28}$Arg$^{26,34}$Lys$^{27}$-GLP-1(7–37); Gly$^8$Asp$^{28}$Arg$^{26,34}$Lys$^{27}$-GLP-1(7–38); Gly$^8$Asp$^{26}$Arg$^{26,34}$Lys$^{27}$-GLP-1(7–38); Arg$^{26,34}$Lys$^{18}$-GLP-1(7–36); Arg$^{26,34}$Lys$^{18}$-GLP-1(7–36)amide; Arg$^{26,34}$Lys$^{18}$-GLP-1(7–37); Arg$^{26,34}$Lys$^{18}$-GLP-1(7–38); Val$^8$Asp$^{19}$Arg$^{26,34}$Lys$^{18}$-GLP-1(7–36); Val$^8$Asp$^{17}$Arg$^{26,34}$Lys$^{18}$-GLP-1(7–36); Val$^8$Asp$^{19}$Arg$^{26,34}$Lys$^{18}$-GLP-1(7–36)amide; Val$^8$Asp$^{17}$Arg$^{26,34}$Lys$^{18}$-GLP-1(7–36)amide; Val$^8$Asp$^{19}$Arg$^{26,34}$Lys$^{18}$GLP-1(7–37); Val$^8$Asp$^{19}$Arg$^{26,34}$Lys$^{18}$GLP-1(7–38); Val$^8$Asp$^{17}$Arg$^{26,34}$Lys$^{18}$GLP-1(7–38); Arg$^{26,34}$Lys$^{23}$-GLP-1(7–36); Arg$^{26,34}$Lys$^{23}$-GLP-1(7–36)amide; Arg$^{26,34}$Lys$^{23}$-GLP-1(7–37); Arg$^{26,34}$Lys$^{23}$GLP-1(7–38); Val$^8$Asp$^{24}$Arg$^{26,34}$Lys$^{23}$-GLP-1(7–36); Val$^8$Asp$^{22}$Arg$^{26,34}$Lys$^{23}$-GLP-1(7–36); Val$^8$Asp$^{24}$Arg$^{26,34}$Lys$^{23}$-GLP-1(7–36)amide; Val$^8$Asp$^{22}$Arg$^{26,34}$Lys$^{23}$-GLP-1(7–36)amide; Val$^8$Asp$^{24}$Arg$^{26,34}$Lys$^{23}$GLP-1(7–37); Val$^8$Asp$^{24}$Arg$^{26,34}$Lys$^{23}$GLP-1(7–38); Val$^8$Asp$^{22}$Arg$^{26,34}$Lys$^{23}$GLP-1(7–38); Arg$^{26,34}$Lys$^{27}$-GLP-1(7–36); Arg$^{26,34}$Lys$^{27}$-GLP-1(7–36)amide; Arg$^{26,34}$Lys$^{27}$-GLP-1(7–37); Arg$^{26,34}$Lys$^{27}$GLP-1(7–38); Val$^8$Asp$^{28}$Arg$^{26,34}$Lys$^{27}$-GLP-1(7–36); Val$^8$Asp$^{26}$Arg$^{26,34}$Lys$^{27}$-GLP-1(7–36); Val$^8$Asp$^{28}$Arg$^{26,34}$Lys$^{27}$-GLP-1(7–36)amide; Val$^8$Asp$^{26}$Arg$^{26,34}$Lys$^{27}$-GLP-1(7–36)amide; Val$^8$Asp$^{28}$Arg$^{26,34}$Lys$^{27}$GLP-1(7–37); Val$^8$Asp$^{28}$Arg$^{26,34}$Lys$^{27}$GLP-1(7–38); Val$^8$Asp$^{26}$Arg$^{26,34}$Lys$^{27}$GLP-1(7–38); Arg$^{26,34}$Lys$^{18}$-GLP-1(7–36); Arg$^{26,34}$Lys$^{18}$-GLP-1(7–36)amide; Arg$^{26,34}$Lys$^{18}$-GLP-1(7–37); Arg$^{26,34}$Lys$^{18}$GLP-1(7–38); Ser$^8$Asp$^{19}$Arg$^{26,34}$Lys$^{18}$-GLP-1(7–36); Ser$^8$Asp$^{17}$Arg$^{26,34}$Lys$^{18}$-GLP-1(7–36); Ser$^8$Asp$^{19}$Arg$^{26,34}$Lys$^{18}$-GLP-1(7–36)amide; Ser$^8$Asp$^{17}$Arg$^{26,34}$Lys$^{18}$-GLP-1(7–36)amide; Ser$^8$Asp$^{19}$Arg$^{26,34}$Lys$^{18}$-GLP-1(7–37); Ser$^8$Asp$^{19}$Arg$^{26,34}$Lys$^{18}$GLP-1(7–38); Ser$^8$Asp$^{17}$Arg$^{26,34}$Lys$^{18}$GLP-1(7–38); Arg$^{26,34}$Lys$^{23}$-GLP-1(7–36); Arg$^{26,34}$Lys$^{23}$-GLP-1(7–36)amide; Arg$^{26,34}$Lys$^{23}$-GLP-1(7–37); Arg$^{26,34}$Lys$^{23}$GLP-1(7–38); Ser$^8$Asp$^{24}$Arg$^{26,34}$Lys$^{23}$GLP-1(7–36); Ser$^8$Asp$^{22}$Arg$^{26,34}$Lys$^{23}$GLP-1(7–36); Ser$^8$Asp$^{24}$Arg$^{26,34}$Lys$^{23}$-GLP-1(7–36)amide; Ser$^8$Asp$^{22}$Arg$^{26,34}$Lys$^{23}$-GLP-1(7–36)amide; Ser$^8$Asp$^{24}$Arg$^{26,34}$Lys$^{23}$GLP-1(7–37); Ser$^8$Asp$^{24}$Arg$^{26,34}$Lys$^{23}$GLP-1(7–38); Ser$^8$Asp$^{22}$Arg$^{26,34}$Lys$^{23}$GLP-1(7–38); Arg$^{26,34}$Lys$^{27}$-GLP-1(7–36); Arg$^{26,34}$Lys$^{27}$-GLP-1(7–36)amide; Arg$^{26,34}$Lys$^{27}$-GLP-1(7–37); Arg$^{26,34}$Lys$^{27}$GLP-1(7–38); Ser$^8$Asp$^{28}$Arg$^{26,34}$Lys$^{27}$-GLP-1(7–36); Ser$^8$Asp$^{26}$Arg$^{26,34}$Lys$^{27}$-GLP-1(7–36); Ser$^8$Asp$^{28}$Arg$^{26,34}$Lys$^{27}$-GLP-1(7–36)amide; Ser$^8$Asp$^{26}$Arg$^{26,34}$Lys$^{27}$-GLP-1(7–36)amide; Ser$^8$Asp$^{28}$Arg$^{26,34}$Lys$^{27}$GLP-1(7–37); Ser$^8$Asp$^{28}$Arg$^{26,34}$Lys$^{27}$GLP-1(7–38); Ser$^8$Asp$^{26}$Arg$^{26,34}$Lys$^{27}$GLP-1(7–38); Arg$^{26,34}$Lys$^{18}$-GLP-1(7–36); Arg$^{26,34}$Lys$^{18}$-GLP-1(7–36)amide; Arg$^{26,34}$Lys$^{18}$-GLP-1(7–37); Arg$^{26,34}$Lys$^{18}$GLP-1(7–38); Thr$^8$Asp$^{19}$Arg$^{26,34}$Lys$^{18}$-GLP-1(7–36); Thr$^8$Asp$^{17}$Arg$^{26,34}$Lys$^{18}$-GLP-1(7–36); Thr$^8$Asp$^{19}$Arg$^{26,34}$Lys$^{18}$-GLP-1(7–36)amide; Thr$^8$Asp$^{17}$Arg$^{26,34}$Lys$^{18}$-GLP-1(7–36)amide; Thr$^8$Asp$^{19}$Arg$^{26,34}$Lys$^{18}$GLP-1(7–37); Thr$^8$Asp$^{19}$Arg$^{26,34}$Lys$^{18}$GLP-1(7–38); Thr$^8$Asp$^{17}$Arg$^{26,34}$Lys$^{18}$GLP-1(7–38); Arg$^{26,34}$Lys$^{23}$-GLP-1(7–36); Arg$^{26,34}$Lys$^{23}$-GLP-1(7–36)amide; Arg$^{26,34}$Lys$^{23}$-GLP-1(7–37); Arg$^{26,34}$Lys$^{23}$GLP-1(7–38); Thr$^8$Asp$^{24}$Arg$^{26,34}$Lys$^{23}$-GLP-1(7–36); Thr$^8$Asp$^{22}$Arg$^{26,34}$Lys$^{23}$-GLP-1(7–36); Thr$^8$Asp$^{24}$Arg$^{26,34}$Lys$^{23}$-GLP-1(7–36)amide; Thr$^8$Asp$^{22}$Arg$^{26,34}$Lys$^{23}$-GLP-1(7–36)amide; Thr$^8$Asp$^{24}$Arg$^{26,34}$Lys$^{23}$GLP-1(7–37); Thr$^8$Asp$^{24}$Arg$^{26,34}$Lys$^{23}$GLP-1(7–38); Thr$^8$Asp$^{22}$Arg$^{26,34}$Lys$^{23}$GLP-1(7–38); Arg$^{26,34}$Lys$^{27}$-GLP-1(7–36); Arg$^{26,34}$Lys$^{27}$-GLP-1(7–36)amide; Arg$^{26,34}$Lys$^{27}$-GLP-1(7–37); Arg$^{26,34}$Lys$^{27}$GLP-1(7–38); Thr$^8$Asp$^{28}$Arg$^{26,34}$Lys$^{27}$-GLP-1(7–36); Thr$^8$Asp$^{26}$Arg$^{26,34}$Lys$^{27}$-GLP-1(7–36); Thr$^8$Asp$^{28}$Arg$^{26,34}$Lys$^{27}$-GLP-1(7–36)amide; Thr$^8$Asp$^{26}$Arg$^{26,34}$Lys$^{27}$-GLP-1(7–36)amide; Thr$^8$Asp$^{28}$Arg$^{26,34}$Lys$^{27}$-GLP-1(7–37); Thr$^8$Asp$^{28}$Arg$^{26,34}$Lys$^{27}$GLP-1(7–38); Thr$^8$Asp$^{26}$Arg$^{26,34}$Lys$^{27}$GLP-1(7–38).

In a further embodiment of the GLP-1 derivative, the parent peptide is: Arg$^{26}$Lys$^{36}$-GLP-1(7–36); Arg$^{34}$Lys$^{36}$-GLP-1(7–36); Arg$^{26}$Lys$^{36}$-GLP-1(7–37); Arg$^{34}$Lys$^{36}$-GLP-1(7–37); Arg$^{26}$Lys$^{37}$-GLP-1(7–37); Arg$^{34}$Lys$^{37}$-GLP-1(7–37); Arg$^{26}$Lys$^{39}$-GLP-1(7–39); Arg$^{34}$Lys$^{39}$-GLP-1(7–39); Arg$^{26,34}$Lys$^{36,39}$-GLP-1(7–39); Arg$^{26}$Lys$^{18}$-GLP-1(7–36); Arg$^{34}$Lys$^{18}$-GLP-1(7–36); Arg$^{26}$Lys$^{18}$GLP-1(7–37); Arg$^{34}$Lys$^{18}$GLP-1(7–37); Arg$^{26}$Lys$^{18}$GLP-1(7–38); Arg$^{34}$Lys$^{18}$GLP-1(7–38); Arg$^{26}$Lys$^{18}$GLP-1(7–39); Arg$^{34}$Lys$^{18}$GLP-1(7–39); Arg$^{26}$Lys$^{23}$-GLP-1(7–36); Arg$^{34}$Lys$^{23}$-GLP-1(7–36); Arg$^{26}$Lys$^{23}$GLP-1(7–37); Arg$^{34}$Lys$^{23}$GLP-1(7–37); Arg$^{26}$Lys$^{23}$GLP-1(7–38); Arg$^{34}$Lys$^{23}$GLP-1(7–38); Arg$^{26}$Lys$^{23}$GLP-1(7–39); Arg$^{34}$Lys$^{23}$GLP-1(7–39); Arg$^{26}$Lys$^{27}$-GLP-1(7–36); Arg$^{34}$Lys$^{27}$-GLP-1(7–36); Arg$^{26}$Lys$^{27}$-GLP-1(7–37); Arg$^{34}$Lys$^{27}$-GLP-1(7–37); Arg$^{26}$Lys$^{27}$GLP-1(7–38); Arg$^{34}$Lys$^{27}$GLP-1(7–38); Arg$^{26}$Lys$^{27}$GLP-1(7–39); Arg$^{34}$Lys$^{27}$GLP-1(7–39); Arg$^{26,34}$Lys$^{18,36}$-GLP-1(7–36); Arg$^{26,34}$Lys$^{18}$GLP-1(7–37); Arg$^{26,34}$Lys$^{18,37}$GLP-1(7–37); Arg$^{26,34}$Lys$^{18,38}$GLP-1(7–38); Arg$^{26,34}$Lys$^{18,39}$GLP-1(7–39); Arg$^{26,34}$Lys$^{18,36}$GLP-1(7–36); Arg$^{26,34}$Lys$^{23}$GLP-1(7–37); Arg$^{26,34}$Lys$^{23,37}$GLP-1(7–37); Arg$^{26,34}$Lys$^{23,34}$GLP-1(7–38); Arg$^{26,34}$Lys$^{23,39}$GLP-1(7–39); Arg$^{26,34}$Lys$^{27,36}$-GLP-1(7–36); Arg$^{26,34}$Lys$^{27}$GLP-1(7–37); Arg$^{26,34}$Lys$^{27,37}$GLP-1(7–37); Arg$^{26,34}$Lys$^{27,38}$GLP-1(7–38); Arg$^{26,34}$Lys$^{27,39}$GLP-1(7–39); Gly$^8$GLP-1(7–36); Gly$^8$GLP-1(7–37); Gly$^8$GLP-1(7–38); Gly$^8$GLP-1(7–39) Gly$^8$Arg$^{26}$Lys$^{36}$-GLP-1(7–36); Gly$^8$Arg$^{34}$Lys$^{36}$-GLP-1(7–36); Gly$^8$Arg$^{26}$Lys$^{36}$-GLP-1(7–37); Gly$^8$Arg$^{34}$Lys$^{36}$-GLP-1(7–37); Gly$^8$Arg$^{26}$Lys$^{37}$-GLP-1(7–37); Gly$^8$Arg$^{34}$Lys$^{37}$-GLP-1(7–37); Gly$^8$Arg$^{26}$Lys$^{39}$-GLP-1(7–39); Gly$^8$Arg$^{34}$Lys$^{39}$-GLP-1(7–39); Gly$^8$Arg$^{26,34}$Lys$^{39}$-GLP-1(7–39); Gly$^8$Arg$^{26}$Lys$^{18}$-GLP-1(7–36); Gly$^8$Arg$^{34}$Lys$^{18}$-GLP-1(7–36); Gly$^8$Arg$^{26}$Lys$^{18}$-GLP-1(7–37); Gly$^8$Arg$^{34}$Lys$^{18}$GLP-1(7–37); Gly$^8$Arg$^{26}$Lys$^{18}$GLP-1(7–38); Gly$^8$Arg$^{34}$Lys$^{18}$GLP-1(7–38); Gly$^8$Arg$^{26}$Lys$^{18}$GLP-1(7–39); Gly$^8$Arg$^{34}$Lys$^{18}$GLP-1(7–39); Gly$^8$Arg$^{26}$Lys$^{23}$-GLP-1(7–36); Gly$^8$Arg$^{34}$Lys$^{23}$-GLP-1(7–36); Gly$^8$Arg$^{26}$Lys$^{23}$GLP-1(7–37); Gly$^8$Arg$^{34}$Lys$^{23}$GLP-1(7–37); Gly$^8$Arg$^{26}$Lys$^{23}$GLP-1(7–38); Gly$^8$Arg$^{34}$Lys$^{23}$GLP-1(7–38); Gly$^8$Arg$^{26}$Lys$^{23}$GLP-1(7–39); Gly$^8$Arg$^{34}$Lys$^{23}$GLP-1(7–39); Gly$^8$Arg$^{26}$Lys$^{27}$-GLP-1(7–36); Gly$^8$Arg$^{34}$Lys$^{27}$-GLP-1(7–36); Gly$^8$Arg$^{26}$Lys$^{27}$GLP-1(7–37); Gly$^8$Arg$^{34}$Lys$^{27}$GLP-1(7–37); Gly$^8$Arg$^{26}$Lys$^{27}$GLP-1(7–38); Gly$^8$Arg$^{34}$Lys$^{27}$GLP-1(7–38); Gly$^8$Arg$^{26}$Lys$^{27}$GLP-1(7–39); Gly$^8$Arg$^{34}$Lys$^{27}$GLP-1(7–39); Gly$^8$Arg$^{26,34}$Lys$^{18,36}$-GLP-1(7–36); Gly$^8$Arg$^{26,34}$Lys$^{18}$GLP-1(7–37); Gly$^8$Arg$^{26,34}$Lys$^{18,37}$GLP-1(7–37); Gly$^8$Arg$^{26,34}$Lys$^{18,38}$GLP-1(7–38); Gly$^8$Arg$^{26,34}$Lys$^{18,39}$GLP-1(7–39); Gly$^8$Arg$^{26,34}$Lys$^{18,36}$-GLP-1(7–36); Gly$^8$Arg$^{26,34}$Lys$^{23}$GLP-1(7–37); Gly$^8$Arg$^{26,34}$Lys$^{23,37}$GLP-1(7–37); Gly$^8$Arg$^{26,34}$Lys$^{23,38}$GLP-1(7–38); Gly$^8$Arg$^{26,34}$Lys$^{23,39}$GLP-1(7–39); Gly$^8$Arg$^{26,34}$Lys$^{23,36}$GLP-1(7–36); Gly$^8$Arg$^{26,34}$Lys$^{27}$GLP-1(7–37); Gly$^8$Arg$^{26,34}$Lys$^{27,37}$GLP-1(7–37); Gly$^8$Arg$^{26,34}$Lys$^{27,38}$GLP-1(7–38); Gly$^8$Arg$^{26,34}$Lys$^{27,39}$GLP-1(7–39); Val$^8$GLP-1(7–36); Val$^8$GLP-1(7–37); Val$^8$GLP-1(7–38); Val$^8$GLP-1(7–39); Val$^8$Arg$^{26}$Lys$^{36}$-GLP- 1(7–36); Val$^8$Arg$^{34}$Lys$^{36}$-GLP-1(7–36); Val$^8$Arg$^{26}$Lys$^{36}$-GLP-1(7–37); Val$^8$Arg$^{34}$Lys$^{36}$-GLP-1(7–37); Val$^8$Arg$^{26}$Lys$^{37}$-GLP-1(7–37); Val$^8$Arg$^{34}$Lys$^{37}$-GLP-1(7–37); Val$^8$Arg$^{26}$Lys$^{39}$-GLP-1(7–39); Val$^8$Arg$^{34}$Lys$^{39}$-GLP-1(7–39); Val$^8$Arg$^{26,34}$Lys$^{36,39}$-GLP-1(7–39); Val$^8$Arg$^{26}$Lys$^{18}$-GLP-1(7–36); Val$^8$Arg$^{34}$Lys$^{18}$-GLP-1(7–36); Val$^8$Arg$^{26}$Lys$^{18}$GLP-1(7–37); Val$^8$Arg$^{34}$Lys$^{18}$GLP-1(7–37); Val$^8$Arg$^{26}$Lys$^{18}$GLP-1(7–38); Val$^8$Arg$^{34}$Lys$^{18}$GLP-1(7–38); Val$^8$Arg$^{26}$Lys$^{18}$GLP-1(7–39); Val$^8$Arg$^{34}$Lys$^{18}$GLP-1(7–39); Val$^8$Arg$^{26}$Lys$^{23}$-GLP-1(7–36); Val$^8$Arg$^{34}$Lys$^{23}$-GLP-1(7–36); Val$^8$Arg$^{26}$Lys$^{23}$-GLP-1(7–37); Val$^8$Arg$^{34}$Lys$^{23}$-GLP-1(7–37); Val$^8$Arg$^{26}$Lys$^{23}$-GLP-1(7–38); Val$^8$Arg$^{34}$Lys$^{23}$-GLP-1(7–38); Val$^8$Arg$^{26}$Lys$^{23}$-GLP-1(7–39); Val$^8$Arg$^{34}$Lys$^{23}$-GLP-1(7–39); Val$^8$Arg$^{26}$Lys$^{27}$-GLP-1(7–36); Val$^8$Arg$^{34}$Lys$^{27}$-GLP-1(7–36); Val$^8$Arg$^{26}$Lys$^{27}$-GLP-1(7–37); Val$^8$Arg$^{34}$Lys$^{27}$GLP-1(7–37); Val$^8$Arg$^{26}$Lys$^{27}$-GLP-1(7–38); Val$^8$Arg$^{34}$Lys$^{27}$GLP-1(7–38); Val$^8$Arg$^{26}$Lys$^{27}$GLP-1(7–39); Val$^8$Arg$^{34}$Lys$^{27}$GLP-1(7–39); Val$^8$Arg$^{26,34}$Lys$^{18,36}$-GLP-1(7–36); Val$^8$Arg$^{26,34}$Lys$^{18}$GLP-1(7–37); Val$^8$Arg$^{26,34}$Lys$^{18,37}$GLP-1(7–37); Val$^8$Arg$^{26,34}$Lys$^{18,38}$GLP-1(7–38); Val$^8$Arg$^{26,34}$Lys$^{18,39}$GLP-1(7–39); Val$^8$Arg$^{26,34}$Lys$^{23,36}$GLP-1(7–36); Val$^8$Arg$^{26,34}$Lys$^{23}$GLP-1(7–37); Val$^8$Arg$^{26,34}$Lys$^{23,37}$GLP-1(7–37); Val$^8$Arg$^{26,34}$Lys$^{23,38}$GLP-1(7–38); Val$^8$Arg$^{26,34}$Lys$^{23,39}$GLP-1(7–39); Val$^8$Arg$^{26,34}$Lys$^{27,36}$GLP-1(7–36); Val$^8$Arg$^{26,34}$Lys$^{27}$GLP-1(7–37); Val$^8$Arg$^{26,34}$Lys$^{27,37}$GLP-1(7–37); Val$^8$Arg$^{26,34}$Lys$^{27,38}$GLP-1(7–38); Val$^8$Arg$^{26,34}$Lys$^{27,39}$GLP-1(7–39).

GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.) which are included herein by reference.

However, protracted acting GLP-1 derivatives, in particular those described in WO 98/08871 are more preferred. The most preferred GLP-1 derivatives are those in which the parent peptide has the formula GLP-1(7-C), wherein C is 36, 37, 38, 39, 40, 41, 42, 43, 44 and 45, wherein optionally a total of up to fifteen, preferably up to ten amino acid residues have been exchanged with any α-amino acid residue which can be coded for by the genetic code, said parent peptide comprising one or two lipophilic substituents having 4 to 40 carbon atoms, preferably from 8 to 25 carbon atoms, optionally via a spacer (such as γ-Glu or β-Ala). The substituents are preferably selected from acyl groups of straight-chained or branched fatty acids.

GLP-1 analogues and derivatives that include an N-terminal imidazole group and optionally an unbranched $C_6$–$C_{10}$ acyl group attached to the lysine residue in position$^{34}$ are also embodiments of the invention.

In a still further embodiment of the invention the GLP-1 agonist is selected from exendin as well as analogs, derivatives, and fragments thereof, e.g. exendin-3 and -4.

Examples of exendin as well as analogs, derivatives, and fragments thereof to be included within the present invention are those disclosed in WO 9746584 and U.S. Pat. No. 5,424,286. U.S. Pat. No. 5,424,286 describes a method for stimulating insulin release with exendin polypeptide(s). The exendin polypeptides disclosed include HGEGTFTSDLSKQMEEEAVRLFIEWLKNGGX; wherein X=P or Y, and HX1X2GTFITSDLSKQMEEEAVRLFIEWLKNGGPSSGAPPPS; wherein X1X2=SD (exendin-3) or GE (exendin-4)). The exendin-3 and -4 and fragments are useful in treatment of diabetes mellitus (types I or II) and prevention of hyperglycaemia. They normalise hyperglycaemia through glucose-dependent, insulin-independent and insulin-dependent mechanisms. Exendin-4 is specific for exendin receptors, i.e. it does not interact with vasoactive intestinal peptide receptors. WO 9746584 describes truncated versions of exendin peptide(s) for treating diabetes. The disclosed peptides increase secretion and biosynthesis of insulin, but reduce those of glucagon. The truncated peptides can be made more economically than fill length versions.

In a still further embodiment of the invention the GLP-1 agonist is a non-peptide.

In a further embodiment the GLP-1 agonist is a molecule, preferably a non-peptide, which binds to a GLP-1 receptor with an affinity constant, $K_D$, below 1 μM, preferably below 100 nM.

Any possible combination of two or more of the embodiments described herein, is comprised within the scope of the present invention.

The term "GLP-1" means GLP-1(7–37) or GLP-1(7–36) amide.

The term "treatment" is defined, as the management and care of a patient for the purpose of combating the disease, condition, or disorder and includes the administration of a GLP-1 agonist to prevent the onset of the symptoms or complications, or alleviating the symptoms or complications, or eliminating the disease, condition, or disorder. Treatment includes modulate, inhibit, decrease, reduce or arrest beta cell degeneration, such as necrosis or apoptosis of beta cells, in particular the programmed β-cell death known as apoptosis of β-cells as well as prevention of beta cell degeneration, such as necrosis or apoptosis of beta cells, in particular prevention of apoptosis of β-cells The term "beta cell degeneration" is intended to mean loss of beta cell function, beta cell dysfunction, and death of beta cells, such as necrosis or apoptosis of beta cells.

In the present context "a GLP-1 agonist" is intended to indicate a molecule, preferably GLP-1 or an analogue or a derivative thereof, or exendin or an analogue or a derivative thereof, or a non-peptide, which binds to a GLP-1 receptor with an affinity constant, $K_D$, below 1 μM, preferably below 100 nM. Methods for identifying GLP-1 agonists are described in WO 93/19175 (Novo Nordisk A/S).

In the present context "a GLP-1 agonist" is also intended to comprise active metabolites and prodrugs thereof, such as active metabolites and prodrugs of GLP-1 or an analogue or a derivative thereof, or exendin or an analogue or a derivative thereof, or a non-peptide. A "metabolite" is an active derivative of a GLP-1 agonist produced when the GLP-1 agonist is metabolized. A "prodrug" is a compound which is either metabolized to a GLP-1 agonist or is metabolized to the same metabolite(s) as a GLP-1 agonist.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either in the peptide, at the N-terminal end or at the C-terminal end of the parent peptide, or any combination thereof.

The term "derivative" is used in the present text to designate a peptide in which one or more of the amino acid residues of the parent peptide have been chemically modified, e.g. by alkylation, acylation, ester formation or amide formation.

The term "a GLP-1 derivative" is used in the present text to designate a derivative of GLP-1 or an analogue thereof. In the present text, the parent peptide from which such a derivative is formally derived is in some places referred to as the "GLP-1 moiety" of the derivative.

For a description of suitable dosage forms, dosage ranges, pharmaceutical formulations etc. reference is made to WO 98/08871 (Novo Nordisk A/S).

The route of administration may be any route, which effectively transports the active compound to the appropriate or desired site of action, such as oral, nasal, pulmonary, transdermal or parenteral.

Pharmaceutical compositions (or medicaments) containing a GLP-1 agonist may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-1 agonist in the form of a nasal or pulmonal spray. As a still further option, the GLP-1 agonist can also be administered transdermally, e.g. from a patch, optionally a iontophoretic patch, or transmucosally, e.g bucally. As a still further option, the GLP-1 agonist (in particular GLP-1 or an analogue thereof) can also be administered by gene therapy, such as by implanting a cell line transformed with a vector such that it secretes the GLP-1 agonist. The implanted cells may be encapsulated in semi permeable membranes, e.g. macro- or microencapsulated. The above mentioned possible ways to administer a GLP-1 agonist are not considered as limiting the scope of the invention.

Pharmaceutical compositions containing a GLP-1 agonist may be prepared by conventional techniques, e.g. as described in Remington's *Pharmaceutical Sciences*, 1985 or in Remington: *The Science and Practice of Pharmacy*, 19$^{th}$ edition, 1995.

Thus, the injectable compositions of the GLP-1 agonist can be prepared using the conventional techniques of the pharmaceutical industry which involves dissolving and mixing the ingredients as appropriate to give the desired end product.

According to one procedure, the GLP-1 agonist is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Further to the above-mentioned components, solutions containing a GLP-1 agonist may also contain a surfactant in order to improve the solubility and/or the stability of the GLP-1 agonist.

A composition for nasal administration of certain peptides may, for example, be prepared as described in European Patent No. 272097 (to Novo Nordisk A/S) or in WO 93/18785.

According to one embodiment of the present invention, the GLP-1 agonist is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 2 mg/ml, preferably not less than about 5 mg/ml, more preferred not less than about 10 mg/ml of the GLP-1 agonist and, preferably, not more than about 100 mg/ml of the GLP-1 agonist.

The GLP-1 agonist can be used in the treatment of various diseases. The particular GLP-1 agonist to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the GLP-1 agonist be determined for each individual patient by those skilled in the art.

EXPERIMENTAL

Example 1

The male Zucker Diabetic Fatty fa/fa (ZDF) rat is a model of Type 2 diabetes. The rats are insulin resistant but normoglycemic from birth and they develop diabetes from about week 7 to week 10 of age. During the transitional period, the animals go through a state of impaired glucose tolerance. Although the animals are hyperinsulinemic before diabetes onset and during the early stages of diabetes, they later lose glucose-stimulated insulin secretion and finally become almost completely insulinopenic.

We have studied the effects of Arg$^{34}$, Lys$^{26}$(N-ε-(γ-Glu (N-α-hexadecanoyl)))-GLP-1(7–37) therapy during a period of time when the animals would normally progress from having impaired glucose tolerance to having overt Type 2 diabetes. Three groups of male ZDF rats (Genetic Models Inc, Indianapolis, Ind., USA) were studied and dosed subcutaneously bi-daily with either vehicle (group A), 30 (group B) or 150 µg/kg (group C) of Arg$^{34}$, Lys$^{26}$(N-ε-(γ-Glu(N-α-hexadecanoyl)))-GLP-1(7–37), n=6 per group. Animals were between 7 and 8 weeks old when dosing was initiated, and fed glucose levels were not different between the groups before dosing began. However, they were elevated compared to a group of non-diabetic Sprague-Dawley rats who had fed glucose levels significantly below the ZDF animals (6.4±0.6 vs 5.8±0.8, mean±SD, p<0.02). This demonstrates the relative impaired glucose tolerant state of the ZDF animals when the study began.

Bromodeoxyuridine (BrDU) is incorporated in newly synthesized DNA and thus will label replicating cells. Six hours before sacrifice the rats were given an injection of 100 mg BrDU/kg intraperitoneally. After sacrifice the pancreata were fixed in 4% PFA, dehydrated, embedded in paraffin, and 3–4 mm sections double stained for BrDU and insulin for the measurement of beta-cell proliferation rate.

Insulin was stained with guinea pig anti-insulin, peroxidase-coupled rabbit anti-guinea pig Ig, and developed with AEC to give a red stain. BrDU was stained by monoclonal mouse anti-BrDU, biotinylated goat anti-mouse Ig, avidin peroxidase, and developed with DAB and CuSO$_4$ to give a dark brown stain. BrDU stained nuclei of cells with insulin stained cytoplasm was examined in more than 1500 cells per section. The examination of the sections were carried out with the origin of the sections blinded to the observer.

The rats treated with Arg$^{34}$, Lys$^{26}$(N-ε-(γ-Glu(N-α-hexadecanoyl)))-GLP-1(7–37) showed a dose dependent increase in the fraction of beta-cells that had incorporated BrDU as a result of stimulated cell proliferation (FIG. 1).

Neighbor sections were stained for insulin and the combination of glucagon-somatostatin-pancreatic polypeptide for the measurement of the relative mass of islet beta-cells and nonbeta-cells. The beta-cells were stained for insulin as described above. The nonbeta-cells were stained with a mixture of monoclonal mouse anti-glucagon+rabbit anti-somatostatin+rabbit anti-pancreatic polypeptide, detected by biotinylated swine anti-multible Ig's, avidin peroxidase, and developed with DAB and CuSO$_4$ to give a dark brown stain. The volume fractions of beta- and nonbeta-cells were estimated by point counting stereologic techniques.

Figure 2:
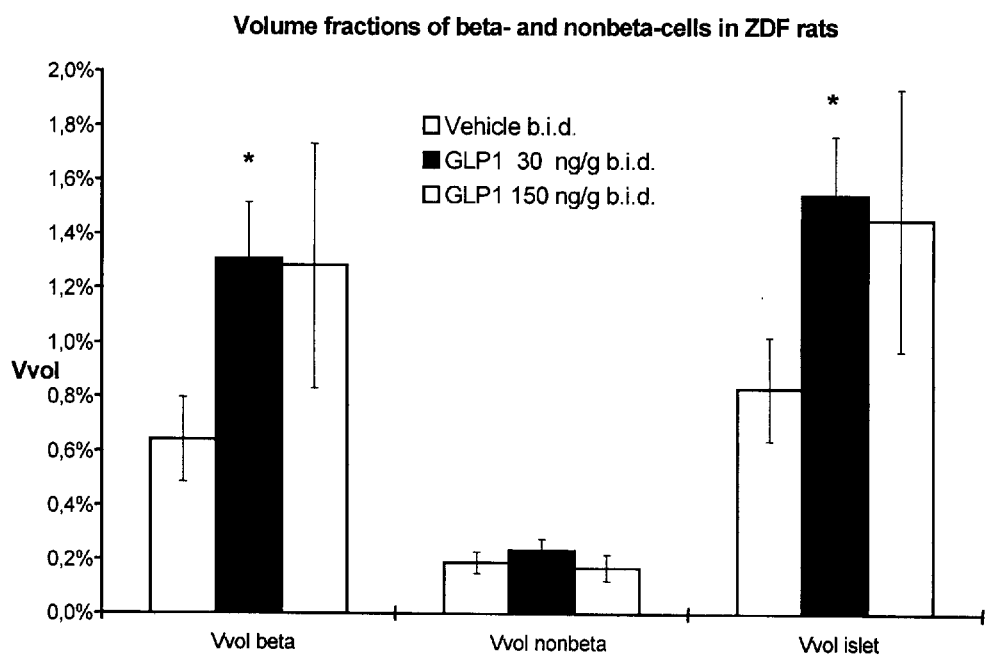
FIG. 2 shows the volume fraction of beta-cells, nonbeta-cells and islets related to total pancreas volume in ZDF rats treated with vehicle, 30 ug/g GLP-1 or 150 ug/g GLP-1.

The beta-cell fraction of the total pancreas was significantly higher in the rats given Arg$^{34}$, Lys$^{26}$(N-ε-(γ-Glu(N-α-hexadecanoyl)))-GLP-1(7–37) at 30 ng/g for 6 weeks compared to vehicle treated rats, while there was no further increase in rats given doses of 150 ng/g (FIG. 2). We have shown that volume of beta-cells after treatment with Arg$^{34}$, Lys$^{26}$(N-ε-(γ-Glu(N-α-hexadecanoyl)))-GLP-1(7–37) increase at a dose (30 ng/g) where proliferation was not seen. This difference strongly indicates that an inhibition of apoptosis facilitated by the administered GLP-1 compound has taken place.

Furthermore, specific inhibition of beta-cell apoptosis by GLP-1 or GLP-1 analogs, that is GLP-1 agonists, can be shown in vitro by measuring inhibition of free fatty acid (FFA), glucose, sulfonylurea, or cytokine induced apoptosis in beta cells.

In vitro assays for characterizing the effect of GLP-1 or analogs thereof on the prevention of beta-cell apoptosis induced by FFA: Briefly, pancreatic islet, e.g. rat, mouse and human, isolated and cultured as described in, e.g. Diabetologia 19, 439, 1980; Transplantation, 68, 597, 1999; J. Mol. Med., 77, 93, 1999, Diabetes 48, 1230, 1999, J. Bio. Chem. 274, 18686, 1999; Proc. Natl. Acad. Sci. 95, 2498, 1999; .J. Bio. Chem, 273, 33501, 1998; Diabetologia 42, 55, 1999, with or without 0.1–10 mM long-chain FFAs (2:1 oleate/palmitate; Sigma) and with GLP-1 or GLP-1 analogs. Characterization of apoptotic beta cells can be analyzed as described below.

In vitro assays for characterizing the effect of GLP-1 or analogs thereof on the prevention of beta-cell apoptosis induced by glucose or sulfonylureas: Briefly, islets can be isolated and cultured as described in J. Bio. Chem, 273, 33501, 1998, and incubated in 0–30 mM glucose as described in. J. Bio. Chem, 273, 33501, 1998, in order to induce apoptosis. In order to prevent the glucose induced apoptosis the islets can be co-incubated with GLP-1 or GLP-1 analogs. Alternatively apoptosis can be induced with 100–500 microM tolbutamide as described in J. Bio. Chem, 273, 33501, 1998. In order to prevent the tolbutamide induced apoptosis the islets can be co-incubated with GLP-1 or GLP-1 analogs. Characterization of apoptotic beta cells can be analyzed as described below and as in J. Bio. Chem, 273, 33501, 1998.

In vitro assays for characterizing the effect of GLP-1 or analogs thereof on the prevention of beta-cell apoptosis induced by cytokines: Briefly, human and rat islets can be isolated and cultured as described in, e.g. Diabetologia 42, 55, 1999. Cytokine induced apoptosis of rat and human beta cells can be done as describe in Diabetologia 42, 55, 1999. In order to prevent the cytokine induced apoptosis the islets can be co-incubated with GLP-1 or GLP-1 analogs. Characterization of apoptotic beta cells can be analyzed as described below and as described in Diabetologia 42, 55, 1999.

Apoptosis and inhibition thereof can be detected in the following way: The free 3' OH strand breaks resulting from DNA degradation which is associated with apoptosis can be detected with the terminal deoxynucleotidyl transferase-mediated dUTP-X3' nick end-labeling (TUNEL) technique (J Cell Biol 199: 493, 1992) or using the following kits e.g. In Situ Cell Death Detection kit; Boehringer Mannheim, Mannheim or ApoTag, Oncor, Gaithersburg, Md.). Preparation of pancreatic sections or islet cultures for apoptosis staining using the TUNEL technique is described in (Diabetologia 42: 566, 1999 and Diabetes 48: 738, 1999).

Apoptosis can also be detected by electrophoresis of the soluble DNA fraction isolated from cultured islets by quantifying the ladder-like appearance as described in (PNAS 95: 2498, 1998).

Finally apoptosis can be detected by double staining of cultured beta cells/islets with the DNA binding dyes Hoechst 33342 and propidium iodide as described in (Diabetologia 42: 55, 1999).

Example 2

Neonatal rats were sacrificed and pancreata were aseptically isolated. Islets of Langerhans were isolated by standard techniques. Intact islets were cultured in 6-well tissue culture plates at 750 islets/well (Nunc, Roskilde, Denmark) with or without 40 U/ml recombinant rat interleukin 1, 100 U/ml interferon-γ, and 100 U/ml tumor necrosis factor-α (all from Peprotech, London, UK) and the indicated doses of the GLP-1 derivative, Arg$^{34}$, Lys$^{26}$(N-ε-(γ-Glu(N-α-hexadecanoyl)))-GLP-1(7–37). After 24 hours of in vitro culture, single cell suspensions were obtained from the islets by gentle triturating in trypsin. After 2 rounds of washing, islet cells were reacted with annexin V-FITC and propedium iodide (PI) using a commercial staining kit according to the manufactures recommendations (Pharmingen, San Diego, Calif., USA). At the end of incubation the samples were analyzed by flow cytometry using a FACScalibur (Becton Dickinson, Mountain View, Calif., USA). Dead cells were excluded by gating on PI-negative cells, 25000 viable cells were acquired per sample. Data were analyzed using the CellQuest software (Becton Dickinson).

Figure 3:
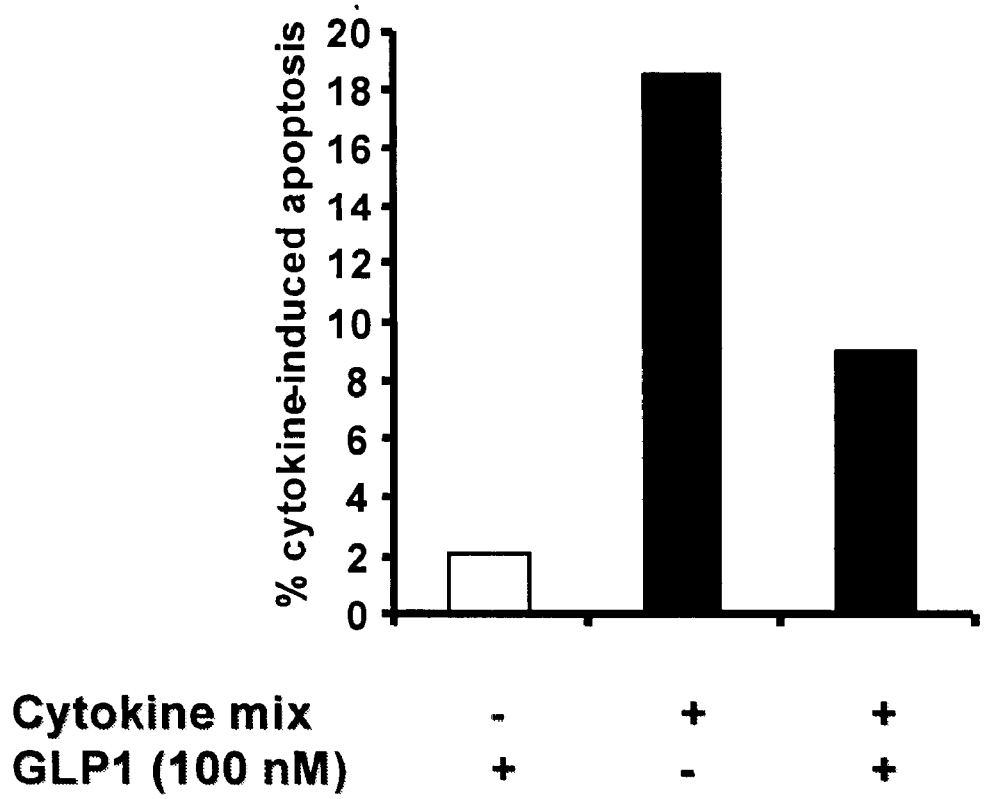
FIG. 3 shouts that 24 hour incubation with a cytokine mix induced a substantial apoptosis in neonatal rat islet cells (middle bar) and that GLP-1 was able to block the cytokine-induced apoptosis in islet cells (far right bar).

FIG. 3 shows that 24 hours incubation with the cytokine mix induced a substantial apoptosis in the neonatal rat islets cells. When islet cells were cultures in the presence of 100 nM of Arg$^{34}$, Lys$^{26}$(N-ε-(γ-Glu(N-α-hexadecanoyl)))-GLP-1(7–37), an approximately 50 % reduction in the cytokine-induced apoptosis was observed. The figure also shows that Arg$^{34}$, Lys$^{26}$(N-ε-(γ-Glu(N-α-hexadecanoyl)))-GLP-1 (7–37) itself had no effect on the level of islet cell apoptosis. These data demonstrate that Arg$^{34}$, Lys$^{26}$(N-ε-(γ-Glu(N-α-hexadecanoyl)))-GLP-1(7–37), is able to block cytokine-induced apoptosis in islet cells ex vivo.

What is claimed is:

1. A method for inhibiting apoptosis of beta cells in vitro, said method comprising contacting said beta cells with an amount of a GLP-1 agonist effective to inhibit apoptosis of said beta cells.

2. The method according to claim 1, wherein said apoptosis of beta cells is induced by a cytokine or a mixture of cytokines selected from the group consisting of interleukin 1 (IL-1), IL-2, IL-3, IL-5, IL-6, IL-7, IL-8, IL-9, IL-12, IL-14, IL-17, interferon-γ, tumor necrosis factor-α, TNF-β, granulocyte macrophage colony stimulating factor, and monocyte chemoattractant protein-1.

3. The method according to claim 2, wherein the cytokines are a mixture of cytokines consisting of IL-1, interferon-γ and tumor necrosis factor-α.

4. The method according to claim 1, wherein the GLP-1 agonist is GLP-1(7–37) or GLP-1(7–36) amide.

5. The method according to claim 1, wherein the GLP-1 agonist is an analogue of GLP-1(7–37), wherein one amino residue of GLP-1(7–37) has been substituted by another amino acid residue.

6. The method according to claim 5, wherein the GLP-1 analogue is a $Val^8$ analogue of GLP-1(7–37).

7. The method according to claim 1, wherein the GLP-1 agonist is a GLP-1 derivative.

8. The method according to claim 7, wherein the GLP-1 derivative has one or more lipophilic substituents.

9. The method according to claim 8, wherein the GLP-1 derivative is a derivative of an analogue of GLP-1(7–37), where one amino residue of GLP-1(7–37) has been substituted by another amino acid residue.

10. The method according to claim 9, wherein the GLP-1 derivative is $Arg^{34}$, $Lys^{26}$(N-ε-(γ-Glu(N-α-hexadecanoyl)))-GLP-1(7–37).

11. A method for inhibiting apoptosis of beta cells in a subject, said method comprising administering to said subject a GLP-1 agonist in an amount effective to inhibit said apoptosis.

12. The method according to claim 11, wherein the GLP-1 agonist is GLP-1(7–37) or GLP-1(7–36) amide.

13. The method according to claim 11, wherein the GLP-1 agonist is an analogue of GLP-1(7–37), wherein one amino residue of GLP-1(7–37) has been substituted by another amino acid residue.

14. The method according to claim 12, wherein the GLP-1 analogue is a $Val^8$ analogue of GLP-1(7–37).

15. The method according to claim 11, wherein the GLP-1 agonist is a GLP-1 derivative.

16. The method according to claim 15, wherein the GLP-1 derivative has one or more lipophilic substituents.

17. The method according to claim 16, wherein the GLP-1 derivative is a derivative of an analogue of GLP-1(7–37) where one amino residue of GLP-1(7–37) has been substituted by another amino acid residue.

18. The method according to claim 17, wherein the GLP-1 derivative is $Arg^{34}$, $Lys^{26}$(N-$\epsilon$-($\gamma$-Glu(N-$\alpha$-hexadecanoyl)))-GLP-1(7–37).

* * * * *